US008604002B1

(12) United States Patent
Walters et al.

(10) Patent No.: US 8,604,002 B1
(45) Date of Patent: Dec. 10, 2013

(54) SACCHARIDE ANTIFREEZE COMPOSITIONS

(75) Inventors: Kent Walters, Notre Dame, IN (US); John G. Duman, Niles, MI (US); Anthony S. Serianni, Notre Dame, IN (US)

(73) Assignee: University of Notre Dame Du Lac, Norte Dame, IN (US)

( * ) Notice: Subject to any disclaimer, the term of this patent is extended or adjusted under 35 U.S.C. 154(b) by 18 days.

(21) Appl. No.: 13/135,065

(22) Filed: Jun. 23, 2011

Related U.S. Application Data

(60) Provisional application No. 61/398,276, filed on Jun. 23, 2010.

(51) Int. Cl.
 *A61K 31/739* (2006.01)
 *C08B 37/00* (2006.01)
 *C09K 3/18* (2006.01)

(52) U.S. Cl.
 USPC .......................... 514/54; 536/123.1; 106/13

(58) Field of Classification Search
 USPC ............... 514/54; 536/123.1; 435/11; 106/13
 See application file for complete search history.

(56) References Cited

U.S. PATENT DOCUMENTS

| 4,448,702 A * | 5/1984 | Kaes ................................ 252/70 |
| 5,627,051 A | 5/1997 | Duman |
| 5,633,451 A | 5/1997 | Duman |
| 2007/0010861 A1 | 1/2007 | Anderson et al. |
| 2008/0317704 A1 | 12/2008 | Obata et al. |
| 2010/0068692 A1 | 3/2010 | Ben et al. |
| 2011/0046615 A1 | 2/2011 | Manstein |
| 2011/0046616 A1 | 2/2011 | Manstein |

OTHER PUBLICATIONS

Walters et al, Proceedings of the National Academy of Sciences, Dec. 1, 2009, 106(48), pp. 20210-2021.*
Abdel-Mawgoud et al., Rhamnolipids: diversity of structures, microbial origins and roles, Appl Microbiol Biotechnol (Mar. 2010) 86:1323-1336.
Walters et al., A nonprotein thermal hysteresis-producing xylomannan antifreeze in the freeze-tolerant Alaskan beetle *Upis ceramboides*, PNAS, Dec. 2009, vol. 106 No. 48, pp. 20210-20215.
Walters, Large Molecular Weight Antifreezes and Related Adaptations in Freeze-Tolerant Alaskan Insects, Ph.D. Dissertation, University of Notre Dame library, Notre Dame, IN, Jul. 2009, 139 pgs.

* cited by examiner

*Primary Examiner* — Shaojia Anna Jiang
*Assistant Examiner* — Ganapathy Krishnan
(74) *Attorney, Agent, or Firm* — Billion & Armitage

(57) ABSTRACT

The invention provides an antifreeze glycolipid compounds and composition comprising a polysaccharide moiety of Formula I:

$$\left[\text{D-Manp} - \text{D-Xylp}\right]_n; \quad (I)$$

wherein D-Manp represents a D-mannopyranose moiety, D-Xylp represents a D-xylopyranose moiety, and n is about 5 to about 70; and one or more lipid moieties covalently linked to the polysaccharide moiety of Formula I or electrostatically associated with the polysaccharide moiety of Formula I. The antifreeze glycolipid compounds and compositions can be used for a variety of industrial, agricultural, medical, and cosmetic applications where recrystallization-inhibition, cyroprotection, or cryopreservation is desired. The antifreeze glycolipid compounds or compositions can be used as, for example, as cryoprotectants for tissue preservation and transplantation, improving the texture of processed frozen food and frozen meats, frostbite protection, crop protection, and green alternatives for land vehicle antifreeze and aircraft de-icing.

26 Claims, 10 Drawing Sheets

SACCHARIDE ANTIFREEZE COMPOSITIONS

RELATED APPLICATIONS

This application claims priority under 35 U.S.C. §119(e) to U.S. Provisional Patent Application No. 61/398,276, filed Jun. 23, 2010, which is incorporated herein by reference.

GOVERNMENT SUPPORT

This invention was made with government support under Grant Nos. OPP-0117104 and IOS-0618342 awarded by the National Science Foundation and Grant No. DE-FG09-93ER-20097 awarded by the Department of Energy. The United States Government has certain rights in the invention.

BACKGROUND OF THE INVENTION

Subzero winter temperatures pose a significant challenge to the survival of organisms in temperate and polar regions. In response, many poikilothermic organisms living in these areas, including fishes, amphibians, reptiles, arthropods, plants, fungi and bacteria, have evolved physiological adaptations to survive subzero temperatures. In a given organism, multiple physiological adaptations permit cold hardiness, including, but not limited to, a subset of the following: accumulation of small molecular mass antifreezes and cryoprotectants, such as sugars and polyhydric alcohols; production of large molecular mass "antifreezes" (e.g., antifreeze proteins (AFPs)); dehydration; production of protein ice nucleators; removal of ice nucleators; and membrane adaptation.

The suite of adaptations that promotes cold hardiness in a given species leads to one of the following overwintering strategies: freeze tolerance or freeze avoidance. Freeze-tolerant organisms survive the formation of extracellular ice, but typically do not survive intracellular freezing. In contrast, freeze-avoiding organisms must avoid freezing or death will result. However, exceptions to this freeze tolerance/freeze avoidance dichotomy are known, including some insect species that can switch overwintering strategies from year-to-year, within a single winter, or even employ both strategies simultaneously in different body compartments. Paradoxically, these alternative overwintering strategies share many of the same physiological adaptations. For example, both freeze-tolerant and freeze-avoiding organisms commonly accumulate polyhydric alcohols and/or large molecular mass antifreezes during cold acclimatization.

The functions of large molecular mass antifreezes, namely antifreeze proteins (AFPs) and antifreeze glycoproteins (AFGPs), are best understood in freeze-avoiding organisms, where these molecules act as "antifreezes" that prevent inoculative freezing and stabilize the supercooled state through the inactivation of ice nucleators. These functions of antifreeze (glyco)proteins (AF(G)Ps) are thought to arise from their ability to interact with the surface of ice crystals and small ice-like clusters of water molecules (embryo crystals) organized by ice nucleators, and thereby inhibit their growth. This adsorption-inhibition mechanism allows AF(G)Ps to depress the freezing point of an ice crystal without significantly affecting its melting point, thus, producing thermal hysteresis (TH), a difference between the melting and freezing points of the ice crystal that is diagnostic for the presence of AF(G)Ps.

Even though TH has been described in multiple freeze-tolerant species, including representative insects, plants, nematodes and fungi, the functions and, in many cases, the chemical structures of the responsible large-molecular-mass antifreezes remain unknown. The modest levels of TH measured, typically 0.2° C.-0.5° C. or less (Duman et al., *J. Insect. Physiol.* 2004, 50: 259-266; Griffiths and Yaish, *Trends Plant Sci.* 2004, 9:399-405), do not appear to prevent the formation of ice. In fact, many freeze-tolerant organisms typically exhibit adaptations that promote freezing at high subzero temperatures, such as extracellular ice-nucleating proteins (Zachariassen and Hammel, *Nature* 1976, 262:285-287). Furthermore, other freeze-tolerant species of arthropods and plants may not exhibit measureable TH in spite of producing large-molecular-mass antifreezes, and instead have only pronounced hexagonal crystal growth and/or recrystallization inhibition, indicating the presence of a low activity and/or low concentration of large-molecular-mass antifreeze.

Even at very low concentrations AF(G)Ps inhibit the recrystallization of ice, thus potentially preventing damage associated with the growth of extracellular ice crystals after the initial freeze. In addition to their "antifreeze" properties, AF(G)Ps possess other functions that rely on their ability to interact with cell membranes. For instance, fish AFGPs and type I AFPs appear to protect cell membranes against the destabilizing effects of low temperatures. AF(G)Ps may also be capable of preventing propagation of ice from the extracellular fluid into the cytosol.

Accordingly, there is a need for the identification and isolation of additional biomolecules that provide thermal hysteresis (TH) properties, and for the structural determination of additional thermal hysteresis factors (THFs). There is also a need for biomolecules that can be applied to human and agricultural uses, such as in compositions that provide cold resistance and freeze resistance properties.

SUMMARY

Until recently, it was thought that all biological large-molecular-mass antifreezes were proteins. The xylomannan antifreeze glycolipid (AFGL) compounds and compositions described herein are the only currently known thermal hysteresis factors (THFs) isolated and purified from a freeze-tolerant animal and the first containing little or no protein. These compounds and compositions can provide cold resistance and freeze resistance properties when applied to a surface, for example, in combination with a suitable topical carrier.

Accordingly, the invention provides an antifreeze glycolipid compound or composition comprising a polysaccharide moiety of Formula I:

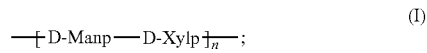

wherein D-Manp represents a D-mannopyranose moiety, D-Xylp represents a D-xylopyranose moiety, and n is about 5 to about 70; and one or more lipid moieties covalently linked to the polysaccharide moiety of Formula I or electrostatically associated with the polysaccharide moiety of Formula I. The mannopyranose and xylopyranose moieties of Formula (I) can be linked to each other via alpha-linkages, beta-linkages, or a combination thereof.

In some embodiments, the mannopyranose and xylopyranose moieties of Formula (I) can be linked via β(1→4) linkages. The polysaccharide moiety of Formula I can be linked to one or more blocks of repeating mannopyranose moieties, xylopyranose moieties, glucopyranose moieties, or combinations thereof. The blocks of repeating sugar moieties can include about 1 to about 20 sugar moieties, or about 1 to about 10 sugar moieties, in each block, and the blocks can optionally be linked to additional moieties of Formula I.

In some embodiments, other sugar moieties can be linked to a moiety of Formula I, and/or to a mannopyranose, xylopyranose block, or glucopyranose block attached to the moiety of Formula I. Various sugar residues can also be included in the overall polysaccharide chain, for example, linked to the moiety of Formula I, or linked to a block of repeating sugar moieties. Examples of such sugar residues include ribose, arabinose, lyxose, allose, altrose, glucose, gulose, idose, galactose, talose, or combinations thereof. In some embodiments, the saccharide chain can include about 10 wt. %, about 15 wt. %, about 20 wt. %, about 25 wt. %, or about 30 wt. % of glucose residues in the chain. One or more hydroxyl groups of the sugar residues of the chain can be optionally methylated.

The ratio of mannopyranose moieties to xylopyranose moieties can be about 20:80 to about 80:20, about 25:75 to about 75:25, or about 40:60 to about 60:40. For example, the ratio of mannopyranose moieties to xylopyranose moieties can be about 20:80, about 25:75, about 40:60, about 50:50, about 60:40, about 75:25, or about 80:20. The sum of the mass of the mannopyranose moieties and xylopyranose moieties can be about 30% to about 99%, about 40% to about 99%, about 50% to about 99%, about 60% to about 99%, about 70% to about 99%, about 80% to about 99%, or about 90% to about 98% of the moiety of Formula I, where the balance of the mass can be the lipid moieties, other sugar moieties, amino acids, or a combination thereof. For example, sum of the mass of the mannopyranose moieties and xylopyranose moieties can be about 30%, about 40%, about 50%, about 60%, about 70%, about 80%, about 90%, about 95%, about 97%, about 98%, or about 99%, where the balance of the mass can be the lipid moieties, other sugar moieties, amino acids, or a combination thereof. The average molecular weight of the antifreeze compounds, such as a compound or composition of Formula I, can be about 1 kDa to about 20 kDa, about 3.2 kDa to about 15 kDa, about 5 kDa to about 10 kDa, about 10 kDa to about 15 kDa, about 5 kDa to about 15 kDa, or about 1.6 kDa to about 6 kDa.

In one embodiment, the polysaccharide moiety of Formula I comprises a glycolipid moiety of Formula II:

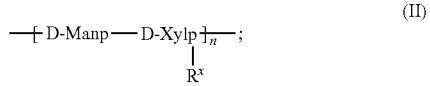

(II)

a glycolipid of Formula III:

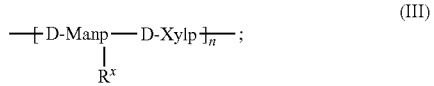

(III)

a glycolipid of Formula IV:

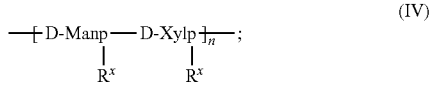

(IV)

or a combination thereof. Each $R^x$ is independently H or a lipid moiety $R^L$ covalently bonded to a saccharide moiety of the formula (e.g., a Manp or Xylp). As used herein, the terms lipid moiety and lipophilic moiety are used interchangeably. Each mannopyranose and xylopyranose can be substituted with one to three $R^x$ groups, at least one $R^x$ on the molecule is $R^L$. The group $R^L$ can be a $(C_6$-$C_{24})$alkyl group, a fatty acid moiety, a mono-, di-, or tri-glyceride, a sterol, or a phospholipid.

In another embodiment, the polysaccharide moiety of Formula I comprises a glycolipid moiety of Formula VI:

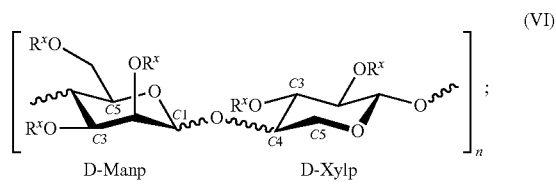

(VI)

wherein each $R^x$ is independently be H or a lipophilic moiety $R^L$, wherein at least one $R^x$ of the molecule is $R^L$.

In another embodiment, the polysaccharide moiety of Formula I comprises a polysaccharide moiety of Formula VII:

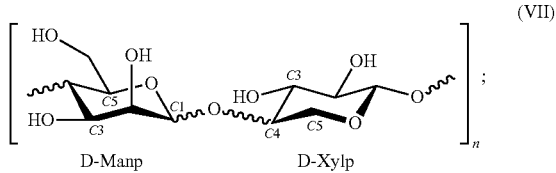

(VII)

where a lipid moiety is electrostatically associated to one or more of the oxygen atoms of the saccharide of Formula VII. The lipid moiety can be an alkyl chain substituted with one or more hydroxyl groups or carboxy groups, a fatty acid, a mono-, di-, or tri-glyceride, a sterol, or a phospholipid.

In various embodiments, one or more of the lipophilic moieties $R^L$ is an alkyl chain (e.g., alkyl chain substituted with one or more hydroxyl groups or carboxy groups), a fatty acid, a mono-, di-, or tri-glyceride, a sterol, or a phospholipid. In some embodiments, one or more of the lipophilic moieties $R^L$ is a fatty acid moiety $R^1$ of the formula —C(=O)R wherein R is a straight chain or branched $(C_8$-$C_{30})$alkyl group. In other embodiments, $R^L$ is an alkyl group of 8-24 carbon atoms, optionally branched, and optionally substituted with one or more hydroxyl groups.

In some embodiments, one or more of the lipophilic moieties $R^L$ is a fatty acid moiety $R^1$ of the formula —C(=O)R wherein R is a straight chain or branched $(C_8$-$C_{30})$alkyl group wherein the alkyl is optionally unsaturated, optionally epoxidized, optionally substituted with one or more hydroxyl groups, or a combination thereof.

In certain specific embodiments, one or more of the lipophilic moieties $R^L$ is a fatty acid moiety $R^1$ wherein $R^1$ is the residue of lauric acid (dodecanoic acid), myristic acid (tetradecanoic acid), palmitic acid (hexadecanoic acid), steric acid (octadecanoic acid), arachidic acid (eicosanoic acid), lignoceric acid (tetracosanoic acid), palmitoleic acid, oleic acid, linoleic acid, linolenic acid, arachidonic acid, or combinations thereof. In other embodiments, $R^L$ is one of the aforementioned fatty acids electrostatically bonded to one of Formulas I-VII.

The antifreeze glycolipid composition can also include one or more lipophilic moieties where $R^L$ is a glyceride moiety having one, two, or three fatty acid substituents. In one embodiment, one or more of the lipophilic moieties $R^L$ is $R^2$ where $R^2$ is a moiety of Formula VIII:

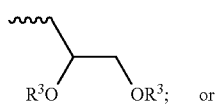

or a moiety of Formula IX:

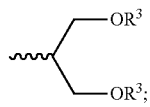

wherein each $R^3$ is independently be H, R, or $R^1$, where R and $R^1$ are as defined above.

In other embodiments, one or more of the lipophilic moieties $R^L$ is a moiety of Formula X:

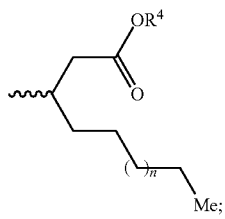

wherein each $R^4$ is independently H, $(C_1-C_7)$alkyl, R, or $R^1$, where R and $R^1$ are as defined above.

In yet another embodiment, one or more of the lipophilic moieties $R^L$ is a moiety of Formula XI:

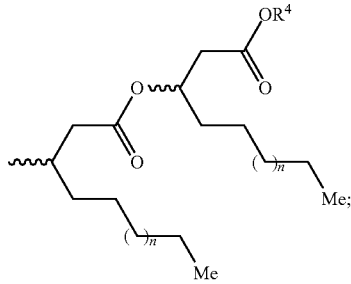

wherein each $R^4$ is independently H, $(C_1-C_7)$alkyl, R, or $R^1$, where R and $R^1$ are as defined above.

In a further embodiment, one or more of the lipophilic moieties $R^L$ is a moiety of Formula XII:

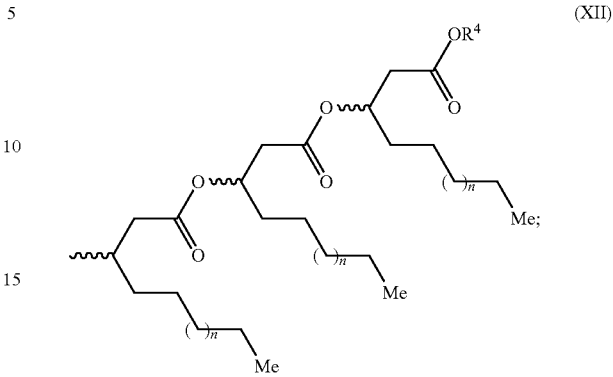

wherein each $R^4$ is independently H, $(C_1-C_7)$alkyl, R, or $R^1$, where R and $R^1$ are as defined above.

In other embodiments, the lipid moiety or lipophilic moiety $R^L$ is covalently bonded to the Formula through an oxygen atom at C2, C3, or C6 of a mannopyranose moiety, at C2 or C3 of a xylopyranose moiety, or a combination thereof.

The antifreeze glycolipid composition can include less than 5 wt. % of amino acids. In some embodiments, the composition includes less than 2 wt. % of amino acids, less than 1 wt. % of amino acids, less than 0.5 wt. % of amino acids, less than 0.1 wt. % of amino acids, or the composition can be free of amino acids.

In some embodiments, the antifreeze glycolipid composition can provide more than 1° C. of thermal hysteresis at a concentration of 5 mg/mL (water). In another embodiment, the antifreeze glycolipid composition can provide more than 2° C. of thermal hysteresis at a concentration of 5 mg/mL. In another embodiment, the composition provides more than 3.5° C. of thermal hysteresis at a concentration of 5 mg/mL. In other embodiments, the antifreeze glycolipid composition provides about 1° C. to about 4° C., or about 1° C. to about 5° C., of thermal hysteresis at a concentration of 5 mg/mL.

The invention also provides a composition comprising a glycolipid composition described above and a pharmaceutically, cosmetically, or agriculturally acceptable carrier. Acceptable carriers include, but are not limited to, water, glycerol, dimethyl sulfoxide, and ethylene glycol. The composition can also include thickeners, wetting agents, preservatives, or combinations thereof.

The invention further provides a method to inhibit ice crystallization comprising contacting the surface of a material in need thereof and an effective amount of an antifreeze glycolipid composition described herein so that ice crystallization is thereby inhibited. The antifreeze glycolipid composition can be added to a material as a cryoprotectant for tissue preservation or as a cryoprotectant for tissue transplantation. The composition can also be added to a material for improving the texture of processed frozen food, for frostbite protection, for plant protection, or it can be added to a composition for land vehicle antifreeze and aircraft de-icing.

The invention also provides a method to inhibit or reduce the severity of frostbite comprising contacting animal skin and an effective amount of an antifreeze glycolipid composition described herein so that the severity of frostbite is reduced or the frostbite is inhibited. The animal can be a human, or alternatively, a farm or companion animal, such as a dog, horse, cow, sheep, goat or pig.

The invention additionally provides a method for reducing ice formation on the surface of a plant comprising contacting the surface of a plant with an effective amount of an antifreeze composition described herein. Another method provides for reducing or preventing propagation of ice into the cells or interstitial cellular space of a plant to protect frost sensitive crops or horticultural plants from damage resulting from frosts, for example, during sensitive growing periods, such as during spring frosts.

The methods can include employing an aqueous spray that includes the antifreeze compounds or compositions described herein. The formulations containing the antifreeze compounds or compositions can include one or more surfactants, such as wetting agents. Such wetting agents can provide suitably good coverage of plant tissues, such as the waxy hydrophobic leaves of some plants.

The compositions of the invention can also include antifreeze proteins or other thermal hysteresis factors in combination with the antifreeze glycolipids described herein. In some embodiments, the antifreeze glycolipids are provided in combination with a liquid carrier such as water, glycerol, or a combination thereof, optionally with other components, as described herein.

The invention therefore provides novel compounds and compositions of the Formulas described herein, intermediates for the synthesis of compounds and compositions of the Formulas, as well as methods of preparing and using the compounds and compositions. The invention also provides compounds of the Formulas described herein that are useful as intermediates for the synthesis of other useful compounds. The invention further provides for the use of the compounds and compositions described herein in topical preparations, such as for reducing ice crystal formation in agricultural applications, for reducing cellular freezing (e.g., frostbite) in fat reduction procedures, and for reducing or avoiding frostbite on skin at cold temperatures.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
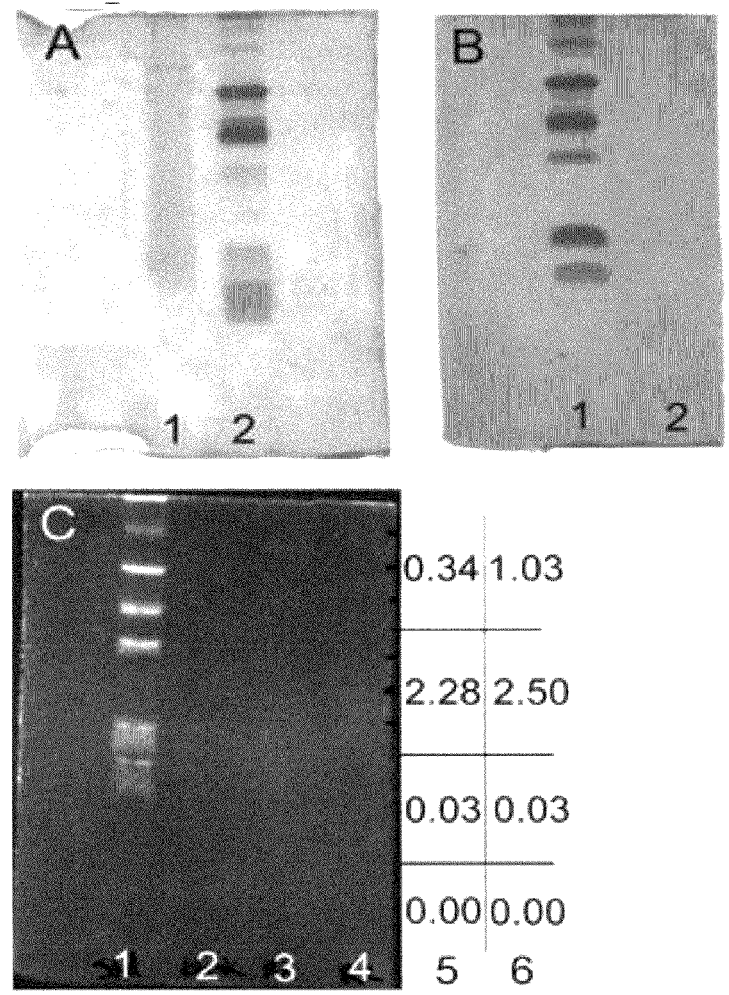
FIG. 1. SDS-PAGE (12%) of R1 (soluble) and R2 (membrane) AFGL fractions from the beetle *Upis ceramboides*. (A) Silver stained gel. Lane assignments: 1, ice purified R1; 2, low molecular weight standards. (B) Silver stained gel. Lane assignments: 1, low molecular weight standards; 2, ice purified R2. (C) Gel stained with Sypro Ruby. Lane assignments: 1, low molecular weight standards; 2, blank (loading dye only); 3, ice purified R1; 4, ice purified R2. Ice purified R1 and R2 were applied to two additional lanes 5 and 6, respectively, which were excised from the gel. Each lane was divided into four segments and the THF was eluted in distilled water overnight. After dialysis, the sample was concentrated and thermal hysteresis (TH) was measured. The TH values (° C.) are shown for lanes 5 and 6 for each gel fragment.

Antifreeze proteins and glycoproteins (AF(G)Ps) were first identified in the blood of Antarctic fishes, where they allow these fish to avoid freezing in ice-laden waters that are colder than the colligative melting point of their body fluids. AF(G)Ps adsorb to the surface of ice and prevent water from joining the crystal lattice, thereby preventing freezing of a solution in the presence of ice until a new, lower (hysteretic) freezing point is reached. Thermal hysteresis (TH), defined as the difference between the colligative melting and hysteretic freezing points, is diagnostic for the presence of large molecular mass antifreezes (e.g., AF(G)Ps).

Since their discovery, AF(G)Ps have been the subjects of active research, ranging from structural biochemistry to ecological physiology and applications in biotechnology. This body of work has revealed the existence of five distinct structural classes of fish AF(G)Ps and demonstrated some unexpected functions of these proteins. In addition to producing TH, all AF(G)Ps appear to prevent the recrystallization of ice, and certain fish AF(G)Ps may protect cell membranes from low-temperature-induced injury.

More recently, TH has been described in additional taxa, representing four kingdoms of life (Duman et al. (2004) *J. Insect. Physiol.* 50:259-266). Structurally distinct AF(G)Ps have been isolated and characterized from plants, insects, collembola, fungi and bacteria, showing that diverse proteins with TH activity have evolved in distantly related cold-tolerant organisms. However, the majority of the responsible thermal hysteresis factors (THFs) have not been isolated or structurally characterized (i.e., their specific chemical compositions have not been determined). In insects, for instance, TH has been identified in over fifty species, but, except for the recently identified AFGLs, AFP sequences have only been published for four of these (Venketesh and Dayananda (2008) *Crit. Rev. Biotechnol.* 28:57-82). Furthermore, TH has been observed in multiple species of freeze-tolerant insects (those able to survive extracellular freezing), but none of the responsible THFs have been structurally characterized. Although the structures of known THFs are extremely diverse and appear to have evolved independently multiple times even within closely related taxa, proteins were the only biomolecules known to produce TH.

Antifreeze Glycolipids (AFGLs).

Antifreeze proteins have the ability to depress the freezing point of water by an unusual non-colligative mechanism, whereby they bind to ice or ice nucleating surfaces to prevent ice growth. Applicants have discovered a nonprotein thermal hysteresis-producing xylomannan glycolipid antifreeze in the freeze-tolerant Alaskan beetle *Upis ceramboides*. In addition to *U. ceramboides*, several other organisms have since been identified that possess the same or similar AFGLs, including other insects, freeze tolerant frogs, and a freeze tolerant plant, *Solanum dulcamara*, also known as the bittersweet nightshade.

Prior to studies of Upis antifreeze glycolipids (AFGLs), this ability to depress the freezing point of water by an unusual non-colligative mechanism had not been identified in molecules other than these special AFPs. The AFGLs are primarily associated with the cell membranes, unlike the AFPs, which are mainly present in the blood of fish or the hemolymph of insects. AFPs, better described as ice-binding factors because they have only minimal thermal hysteresis activity, are also known from some freeze tolerant insects, plants, microorganisms and fungi. As far as was known, all of the antifreeze activity associated with these organisms was thought to be due to protein components.

The AFGLs can function in freeze tolerant organisms in two ways. First, recrystallization, a process whereby large ice crystals become larger over time as smaller crystals get smaller and disappear, is a potentially damaging process in tissue. AFPs are known to be able to prevent it and AFGLs can also do so. Secondly, most of the AFGLs in the organisms studied are present on cell membranes. Consequently, they are perfectly positioned to prevent the spread of ice from the extracellular fluid (where it is tolerated in freeze tolerant species) into the intracellular fluid (cytoplasm), where it is typically lethal.

Because of the second factor described above, the addition of AFGLs to mammalian (or other freeze sensitive) cells, tissues, and the like, prior to freeze preservation, or other means of cryopreservation (vitrification; holding at low, sub-zero temperatures in an unfrozen state) can permit improved cryopreservation of biologically and medically important materials for research, organ and tissue transplant, and other purposes.

AFGL can be isolated and purified from natural sources using membrane extraction followed by ice binding methods, or they can be synthesized by chemical and/or enzymatic procedures. Plants that naturally produce the AFGLs, especially perennials, such as *Solanum dulcamara* (bittersweet nightshade), are favorable sources of these materials. Such plants can be grown as a field of crops, harvested at the appropriate time in the autumn after the AFGLs have been produced, and the AFGLs can then be extracted and purified for use in various antifreeze applications.

Thermal hysteresis (TH), a difference between the melting and freezing points of a solution that is indicative of the presence of large molecular mass antifreezes (e.g., antifreeze proteins), has been described in animals, plants, bacteria and fungi. While all previously described TH-producing biomolecules are proteins, most thermal hysteresis factors (THFs) have not yet been structurally characterized and none have been characterized from a freeze-tolerant animal. A highly active THF from the freeze-tolerant beetle, *Upis ceramboides*, has been isolated by means of ice affinity. Amino acid chromatographic analysis, polyacrylamide gel electrophoresis, UV-Vis spectrophotometry and NMR spectroscopy indicated that the THF contains little or no protein, yet it produced 3.7±0.3° C. of TH at 5 mg/mL, comparable to that of the most active insect antifreeze proteins.

Compositional and structural analyses show that this antifreeze contains a β-mannopyranosyl-(1→4) β-xylopyranose backbone and a fatty acid component, where the lipid can be covalently linked to the saccharide or electrostatically (ionically) bound to the saccharide. Consistent with the structures shown herein, treatment with endo-β-(1→4)xylanase ablated TH activity. This xylomannan is the first TH-producing antifreeze isolated from a freeze-tolerant animal and the first in a new class of highly active THFs that contain little or no protein.

Antifreeze Xylomannan Compositions.

The invention provides antifreeze glycolipid compositions that have little or no proteins associated with them, and that possess significant thermal hysteresis properties. Accordingly, the invention provides an antifreeze glycolipid composition comprising a polysaccharide moiety of Formula I:

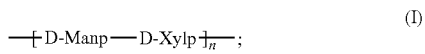

(I)

wherein D-Manp represents a D-mannopyranose moiety, D-Xylp represents a D-xylopyranose moiety, and n is about 5 to about 70; and one or more lipid moieties covalently linked to the polysaccharide moiety of Formula I or electrostatically associated with the polysaccharide moiety of Formula I.

The composition can be a collection of the glycolipid conjugates, or the composition can be a collection of the xylomannan polysaccharide electrostatically associated with lipid moieties, such as fatty acids, for example, through ionic bonding. For example, the composition can include a glycolipid of Formula II:

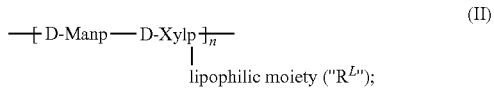

(II)

a glycolipid of Formula III:

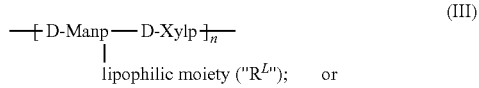

(III)

or a glycolipid of Formula IV:

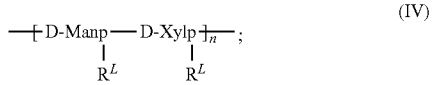

(IV)

wherein lipophilic moiety ($R^L$) is covalently bonded to one of the saccharide components, the other, both, or a combination thereof. The lipid moiety ($R^L$) can be covalently bonded to a saccharide moiety directly (e.g., through an ether or ester group) or it can be bonded to the saccharide moiety through a linking group, such as glycerol.

In other embodiments, the xylomannan polysaccharide can be electrostatically associated with lipid moieties, as represented by Formula V:

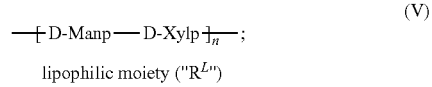

(V)

wherein the lipophilic moiety is, for example, an alkyl chain substituted with one or more hydroxyl groups or carboxy groups, a fatty acid, a mono-, di-, or tri-glyceride, a sterol, or a phospholipid.

In various embodiments, the lipophilic moiety $R^L$ can be any lipid molecule or moiety associated with the saccharide chain, by electrostatic interactions or by direct covalent bonding. The lipid molecule can be, for example, an alkyl chain, a fatty acid, a mono-, di-, or tri-glyceride, a sterol, or a phospholipid. When the lipid molecule is covalently bonded to the saccharide chain, the covalent bonding can be at any hydroxyl group of the saccharide chain (e.g., at C2, C3, C4 when not linked to another sugar moiety, C6, or the anomeric position C1). The conjugation can be present on one or more mannose saccharides, one or more xylose saccharides, or a combination thereof.

In one embodiment, the polysaccharide moiety of Formula I can be a polysaccharide moiety of Formula VI:

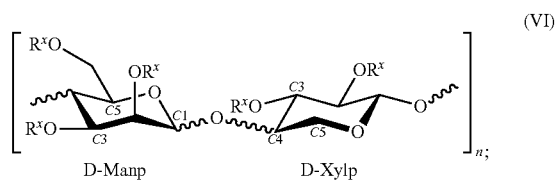

(VI)

where n is about 5 to about 70, and each $R^x$ can independently be H or a lipophilic moiety $R^L$, where at least one $R^x$ of the molecule is $R^L$. When the composition is an electrostatic association of the xylomannan and the lipid moiety, the xylomannan can be a saccharide of Formula VII:

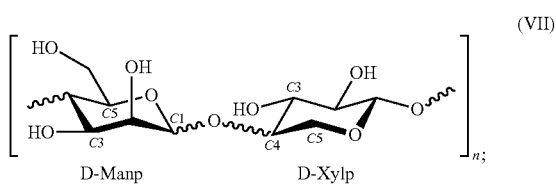

(VII)

where a lipid moiety is electrostatically associated to one or more of the oxygen atoms of the saccharide of Formula VII. The antifreeze xylomannan compositions can also be combinations of the various formulas described herein, such as a combination of a polysaccharide of Formula VI and a polysaccharide of Formula VII, where some lipid moieties are covalently bonded to the polysaccharide and others are ionically associated to the polysaccharide of Formula VI and/or Formula VII.

In various embodiments, the value of n for Formulas I-VII can be about 5 to about 70. For example, n can be about 5, about 10, about 15, about 20, about 25, about 30, about 35, about 40, about 45, about 50, about 55, about 60, about 65, or about 70, or a range from one to any other of the aforementioned integers.

In some embodiments, $R^L$ can be a fatty acid moiety $R^1$ of the formula —C(═O)R wherein R represents an aliphatic group, such as an optionally substituted alkyl group of at least 6 carbons. In some embodiments, R can comprise between about 8 and about 30 carbon atoms. The fatty acid moieties can be saturated, monounsaturated, or polyunsaturated (e.g., having 2 to about 5 sites of unsaturation). In some embodiments, the fatty acid can include one or more hydroxyl substituents and/or sites of epoxidation (e.g., in addition to or in place of a site of unsaturation). In one embodiment, the R group is at least about 8, 9, 10, 11, 12, 13, 14, 15, 16, 17, 18, 19, or 20 carbons in length. R can be a straight or branched chain. The branched chains may have one or more points of branching. In addition, the branched chains may include cyclic branches.

In various embodiments, $R^L$ can be the residue of saturated fatty acid $R^1$ such as lauric acid (dodecanoic acid), myristic acid (tetradecanoic acid), palmitic acid (hexadecanoic acid), steric acid (octadecanoic acid), arachidic acid (eicosanoic acid), or lignoceric acid (tetracosanoic acid); unsaturated acids such as palmitoleic (a C16 acid), and oleic acid (a C18 acid); polyunsaturated acids such as linoleic acid (a di-unsaturated C18 acid), linolenic acid (a tri-unsaturated C18 acid), or arachidonic acid (a tetra-unsubstituted C20 acid), or combinations thereof.

In various other embodiments, one or more $R^L$ groups can be glyceride moieties having fatty acid substituents. For example, one or two fatty acids can be linked to a glyceride moiety to form mono-, or di-glyceride, and the mono- and di-glycerides can be covalently bonded to the xylomannan chain through one of the oxygen substituents of the polysaccharide.

In some embodiments, for example, associated with Formula V or VII, the lipid moiety can be a mono-, di-, or tri-glyceride.

In some embodiments, $R^L$ can be $R^2$ where $R^2$ is a moiety of Formula VIII:

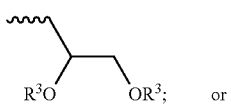

(VIII)

or or Formula IX:

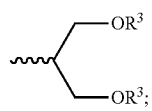

(IX)

where each $R^3$ can independently be H, R, or $R^1$ (i.e., a hydroxyl, an ether, or an ester). Typically, one or more $R^3$ will be other than H, such that the compound possesses suitable thermal hysteresis activity. Thus the glycolipids described herein can have lipid moieties wherein $R^3$ can be an alkanoyl or "fatty acid" moiety. Examples of such moieties include $C_8$-$C_{24}$ alkanoyl groups. The alkanoyl group can be a straight chain or branched. The alkanoyl group can be optionally unsaturated at one, two, or three locations along the carbon chain. Additionally, the alkanoyl group can be optionally substituted with one or more hydroxyl groups or epoxide rings (e.g., in place of a site of unsaturation).

In some embodiments, $R^L$ can be derived from a hydroxyalkanoic acid to form a moiety of Formula X:

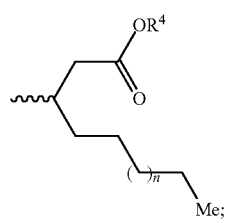

(X)

where the wavy line of Formula X represents the location of a covalent bond to an oxygen residue (e.g., a hydroxyl with the hydrogen removed to add Formula X) of the saccharide backbone Formula I or related xylomannan formulas described above; where each $R^4$ is independently H, ($C_1$-$C_7$) alkyl, R, or $R^1$.

In some embodiments, $R^L$ can be derived from a dimer of a hydroxyalkanoic acid to form a moiety of Formula XI:

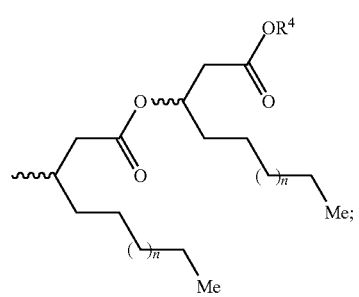

(XI)

or a trimer of a hydroxyalkanoic acid to form a moiety of Formula XII:

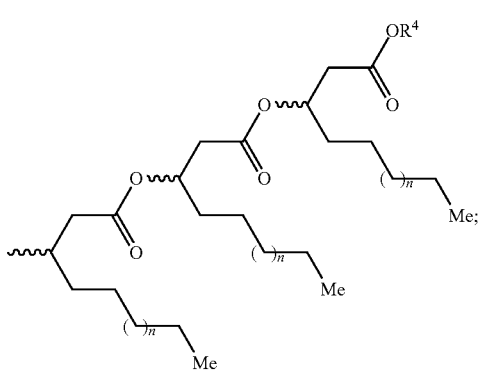

(XII)

where each $R^4$ is independently H, ($C_1$-$C_7$)alkyl, R, or $R^1$.

Applications of Xylomannan Compositions:

Despite overall increases in mean temperatures, an increase in devastating spring frosts is expected due to the erratic weather patterns associated with global climate change. Consequently, there is an increased need to provide fruit and other agricultural crops with effective methods of frost protection. The glycolipid compositions described herein address this need by providing highly active antifreeze glycolipids (AFGLs) that can be formulated into various topical formulations to protect plants such as fruit and other agricultural crops, and any plants in need of protection from frost damage. The compositions are effective because they can lower ice nucleation temperatures and inhibit the propagation of ice in plants. The use of highly active antifreeze glycolipids (AFGLs), optionally in combination with antifreeze proteins (AFPs), represents an economically valuable approach to inhibiting inoculative freezing and enhancing supercooling in herbaceous plants and newly emerging plant parts on perennial plants, such as fruit tree flower buds and flowers.

Because the glycolipid compositions described herein possess significant thermal hysteresis antifreeze properties and when in the presence of cells they adhere to the cell membranes, they can to protect the cells from lethal cytoplasmic freezing initiated by extracellular ice surrounding the cells. In addition, the glycolipid compositions are strong inhibitors of recrystallization. The compositions can also protect cell membranes from low-temperature-induced injury. Accordingly, the compositions therefore can be used in a variety of industrial, agricultural, medical, and cosmetic applications where recrystallization-inhibition or protection of cells and/or tissues from freezing is desired.

Thus the antifreeze glycolipid compositions can be used as recrystallization inhibitors and/or cryopreservants, for example, as a cryoprotectant for tissue preservation and transplantation, improving the texture of processed frozen food and frozen meats, frostbite protection, plant protection, and green alternatives for land vehicle antifreeze and aircraft de-icing.

In some embodiments, the antifreeze glycolipid compositions can be used to enhance the supercooling properties of a fluid to prevent the freezing of fluids at temperatures below their equilibrium melting temperature. The antifreeze glycolipid compounds and compositions can also be used to prevent or limit ice growth or recrystallization of frozen goods, and provide protection from damage that normally would result from freezing biological materials. These effects can be mediated by adding purified AFGLs alone, or alternatively the AFGLs can be combined with other antifreeze components such as antifreeze proteins or glycoproteins.

In some embodiments, the invention provides a method of inhibiting ice crystal growth comprising contacting the surface of a food to be frozen (e.g., fruits, vegetables, meat, sea food, or the like) with a glycolipid composition as described herein, so that ice crystal growth on the surface of the food is inhibited, reduced, or prevented. The composition to be frozen can be a food product such as, for example, ice cream, dough, frozen deserts, frozen pizza, fruits, vegetables, beef, chicken, pork, shrimp, and the like.

Various compositions of the glycolipids can be useful for recrystallization-inhibition in aqueous substances and aqueous based systems, including cells, tissues, food, industrial fluids, and others. In various embodiments, the composition will include a carrier, such as the components of a cream, lotion, ointment, gel, or solution. The term "carrier" refers to any diluent, adjuvant, excipient, or vehicle that can be used to suitably include the glycolipid composition.

In various embodiments, the AFGLs in the formulations can be combined with antifreeze proteins (AFPs) to provide formulations with two or more kinds of antifreeze components. For example, AFGLs or combinations of AFGLs and AFPs (e.g., the combination of *Dendroides canadensis* AFPs and the AFGLs described herein) can be used as sprays on frost tender plants to protect them from inoculative freezing initiated from the plant surfaces. Examples of suitable antifreeze proteins that can be used in the formulation include those described in U.S. Pat. Nos. 5,633,451 (Duman) and 5,627,051 (Duman), the disclosures of which are incorporated herein by reference.

Pharmaceutical, Cosmetic, and Plant Protection Formulations.

The xylomannan antifreeze glycolipid compositions described herein can be used to prepare therapeutic pharmaceutical or cosmetic formulations or preparations. The compounds and compositions can be administered to a mammalian host, such as a human patient, or for example, to inhibit frostbite. Similarly, the formulations can be used to protect frost sensitive crop or horticultural plants from spring frosts. The formulations will typically take the form of a topical preparation, such as a cream, lotion, ointment, gel, solution, or aerosol.

The compositions and preparations typically contain at least 0.1 wt. % of active xylomannan compound or composition (active agent). The percentage of the active agent can vary and may conveniently be from about 0.5 wt. % to about 60 wt. %, about 1 wt. % to about 30 wt. %, about 1 wt. % to about 20 wt. %, or about 1 wt. % to about 10 wt. %, of a given unit dosage form or topical formulation. The amount of active agent in formulations is such that an effective dosage level can be obtained.

For topical administration, compounds may be applied in pure form, however it will generally be desirable to administer the active agent to the skin as a formulation, for example, in combination with a dermatologically acceptable carrier, which may be a solid or a liquid. Thus, the formulation can contain a solid, semi-solid, or liquid carrier. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. Any material used in preparing the formulation should be pharmaceutically or agriculturally acceptable and substantially non-toxic in the amounts employed. In various embodiments, the formulations may contain one or more binders, excipients, disintegrating agents, and lubricants. The proper fluidity can be maintained, for example, by the maintenance of the required particle size, particularly in the case of dispersions, or by the use of surfactants.

Topical formulations of the active agent can be prepared in water, optionally mixed with one or more nontoxic surfactants. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms. For example, the prevention of the action of microorganisms can be brought about by various antibacterial and antifungal agents, for example, parabens, chlorobutanol, phenol, sorbic acid, thiomersal, and the like.

Useful solid carriers include finely divided solids such as talc, clay, microcrystalline cellulose, silica, alumina, and the like. Useful liquid carriers include water, dimethyl sulfoxide (DMSO), alcohols, glycols such as glycerol, or water-alcohol/glycol blends, in which the active agent can be dissolved or dispersed at effective levels, optionally with the aid of non-toxic surfactants. Carriers such as DMSO and glycerol can also help the active agents permeate the epidermis and dermis. The formulations can also include sugars such as sucrose, stachuose, and/or trehalose. Adjuvants such as fragrances and additional antimicrobial agents can be added to optimize the properties for a given use. The resultant liquid or semi-solid formulations can be applied from absorbent pads, used to impregnate bandages and other dressings, or sprayed onto an area using a pump-type or aerosol sprayer. A wetting agent can be included in formulations to achieve suitable coverage of surfaces such as the waxy hydrophobic leaves of some plants. Examples of suitable wetting agents include propylene glycol, Silwet, poloxamer F68, cellulose polymers (carboxymethyl cellulose, hydroxyethylcellulose, methylcellulose), polyvinyl alcohol, dextran, and the like.

Thickeners such as synthetic polymers, fatty acids, fatty acid salts and esters, fatty alcohols, modified celluloses, or modified mineral materials can also be employed with liquid carriers to form spreadable pastes, creams, lotions, gels, ointments, and the like, for application directly to the skin of the user.

Examples of dermatological formulations for delivering active agents to the skin are known to the art; for example, see U.S. Pat. Nos. 4,992,478 (Geria), 4,820,508 (Wortzman), 4,608,392 (Jacquet et al.), and 4,559,157 (Smith et al.). Further reference can be made to "Remington, The Science and Practice of Pharmacy", 21$^{st}$ Ed., David B. Troy, Ed.; 2005, Lippincott Williams & Wilkins; Baltimore, Md. (particularly Part 5: Pharmaceutical Manufacturing); and "Goodman & Gilman's The Pharmacological Basis of Therapeutics", 11$^{th}$ Ed., Laurence L. Brunton, Ed.; 2006, McGraw-Hill Companies, Inc.; New York, N.Y. (particularly Section XIII: Dermatology), for the preparation and use of topical compositions. Such dermatological formulations can be used in combinations with the xylomannan compositions described herein, for example, by using a xylomannan composition described herein in place of the active described in the composition known in the art.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a an alkyl chain or saccharide moiety can refer to one to about five, one to about four, or one to about three, depending on the desired amount of substitution.

The term "about" can refer to a variation off ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a compound or composition described herein, or an amount of a combination of compounds or compositions described herein, e.g., that is effective to treat or prevent a condition such as frostbite, in a host.

Thus, an "effective amount" generally means an amount that provides the desired effect, such as an amount necessary to create thermal hysteresis to reduce the occurrence or severity of frostbite.

The term "thermal hysteresis" refers to difference between the colligative melting and hysteretic freezing points. By definition, the equilibrium melting and freezing points of water are identical. However, the presence of thermal hysteresis factors lowers the non-equilibrium freezing point of water without lowering the melting point (equilibrium freezing point). Thus when thermal hysteresis factors, such as the AFGLs described herein, are added to a solution they produce a difference between the freezing and melting temperatures of the solution, which difference is referred to as "thermal hysteresis".

The terms "treating", "treat" and "treatment" include (i) preventing a condition from occurring (e.g., prophylaxis); (ii) inhibiting the condition or arresting its development; (iii) relieving the condition; and/or (iv) diminishing symptoms associated with the condition. Thus, the terms "treat", "treatment", and "treating" can extend to prophylaxis and include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of an event, such as the formation of ice crystals. The inhibition can be greater than about 20%, 40%, 60%, 80%, 90%, 95%, or 99%, for example, compared to the growth or progression that occurs in the absence of the treatment or contacting.

The term "lipid", "lipid moiety", or "lipophilic moiety" refers to a lipid molecule or residue. The lipid can be, for example, a fatty acid, a phospholipid (such as phosphatidylcholine), a sphingolipid, a sterol, or a residue thereof (i.e., where a hydrogen of the lipid is removed and the residual bond is connected to another molecule, such as a saccharide as described herein).

The term "fatty acid" refers to a carboxylic acid having the formula $RCO_2H$. R represents an aliphatic group, such as an optionally substituted alkyl group. R can comprise between about 8 and about 30 carbon atoms. Fatty acids can be saturated, monounsaturated, or polyunsaturated (e.g., 2 to about 5 sites of unsaturation). In some embodiments, the fatty acid can include one or more hydroxyl substituents and/or sites of epoxidation.

In one embodiment, the R group is at least about 8, 9, 10, 11, 12, 13, 14, 15, 16, 17, 18, 19, or 20 carbons in length. R can be straight or branched chain. The branched chains may have one or more points of branching. In addition, the branched chains may include cyclic branches. Furthermore, R can be saturated or unsaturated. If unsaturated, the R can have one or more points of unsaturation.

Thus, the fatty acids can be saturated, monounsaturated, or polyunsaturated and include varying carbon chain lengths ranging from about $C_8$ to about $C_{30}$, or about $C_{12}$ to about $C_{24}$. Common fatty acid moieties include saturated fatty acids such as lauric acid (dodecanoic acid), myristic acid (tetradecanoic acid), palmitic acid (hexadecanoic acid), steric acid (octadecanoic acid), arachidic acid (eicosanoic acid), and lignoceric acid (tetracosanoic acid); unsaturated acids such as palmitoleic (a C16 acid), and oleic acid (a C18 acid); polyunsaturated acids such as linoleic acid (a di-unsaturated C18 acid), linolenic acid (a tri-unsaturated C18 acid), and arachidonic acid (a tetra-unsubstituted C20 acid). One, two, or three fatty acids can be linked to a glyceride moiety to form mono-, di-, or tri-glycerides. The mono- and di-glycerides can be covalently bonded to the xylomannan chain.

The term "purify," "purified," or "purification" means the removal or isolation of a molecule or complex from its environment by, for example, isolation or separation. "Substantially purified" molecules are at least about 60% free, at least about 75% free, or at least about 90% free from other components with which they are associated. These terms also refer to the removal of contaminants from a sample. For example, the removal of contaminants can result in the absence of proteins from a sample. For example, when a glycolipid is produced in a host cell, the glycolipid composition can be purified by the removal of host cell proteins.

The terms "purify," "purified," and "purification" are relative terms and do not require absolute purity. Thus, for example, when a glycolipid composition is produced in host cells, a purified glycolipid composition is one that is substantially separated from other cellular components (e.g., nucleic acids, polypeptides, other carbohydrates, or other fatty acid derivatives or products). In some embodiments, a glycolipid composition is purified when at least about 80% by weight of a sample is composed of the glycolipid compound or composition. In other embodiments, a glycolipid composition is purified when at least about 85%, 90%, 92%, 95%, 98%, or 99% or more by weight of a sample is composed of the glycolipid compound or composition.

The term "frostbite" refers to a condition where localized injury or damage is caused to skin or other tissues due to extreme cold, typically 0° C. or below. The condition is characterized by cessation of blood circulation in the tissue. Frostbite can cause vasoconstriction and damage to blood vessels, impairing local circulation. The condition can result in a number of signs and symptoms including anoxia, edema, pain, vesiculation, and necrosis. Frostbite often occurs in body parts with large areas exposed to cold temperatures and can spread to subcutaneous tissues. Body parts typically affected by frostbite include the ears, nose, cheeks, fingers, and toes.

The initiating event in frostbite is usually extracellular nucleation of ice in the skin on the face, hands or feet. The rate of ice formation is impacted by ambient temperature and skin exposure. Most commonly the ice grows slowly and there is little ice within the cells, however under extreme conditions the ice forms rapidly and it will be present in both cells and tissues. The lesions can range from frostnip ($1^{st}$ degree), skin freezing and blistering ($2^{nd}$ degree) to involvement of the underlying blood vessels and bone ($3^{rd}$ and $4^{th}$ degree). In late stage frostbite ($3^{rd}$ and $4^{th}$ degree), ice crystals in the affected cells melt causing the cells to lyse, resulting in blister formation. Significant loss of circulation from frostbite can result in gangrene, causing tissue to turn black and dry.

The pathophysiology of frostbite involves three principal mechanisms: direct cellular injury; hypoxia; and release of vasoactive and toxic byproducts of the body's inflammatory response to injury. The primary mechanisms of direct cellular injury are a consequence of extracellular ice formation and/or intracellular ice formation, the consequences of which include mechanical damage, "solution effects" such as cell dehydration, cell shrinkage and abnormal electrolyte concentrations, thermal shock, denaturation of lipid-protein complexes, hypoxia and reperfusion injury. The tissue changes do not manifest until after the tissue has thawed. Thereafter, most of the changes are similar to those observed in reperfusion injuries after periods of hypoxia in tissue and organ systems. Upon thawing the capillaries supplying blood to the skin become dilated and leaky, resulting in accumulation of fluid and protein in the interstitial spaces. Edema formation increases in severity until red blood cell aggregation and thrombosis lead to microcirculatory failure.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Thermal Hysteresis Factors Isolated from *U. ceramboides*

Thermal Hysteresis Factors (THFs) Isolated from *U. ceramboides* are Highly Active and Contain Little or No Protein.

The THFs in adult darkling beetles, *U. ceramboides*, from interior Alaska were investigated because they tolerate freezing to −60° C. in midwinter and were reported to exhibit ~0.4° C. of TH in their hemolymph after cold acclimation (Duman et al., (2004) *J Insect Physiol* 50:259-266). TH values <0.1° C. were typically observed and hexagonal ice crystal morphology only was often detected in the hemolymph of cold adapted insects, indicating the presence of a low concentration of THF and/or a low specific activity THF. The sporadic presence of >0.5° C. of TH in the hemolymph of *U. ceramboides* is consistent with observations on other freeze-tolerant arthropods (Walters et al. (2009) *J. Exp. Biol.* 212:305-312).

To isolate the THF, 40.3 g of cold-acclimated *U. ceramboides* was homogenized and molecules of increasing cell membrane affinity were solubilized in three successive extractions. THFs present in each extract (R1, soluble fraction; R2, first membrane-associated fraction; R3, second membrane-associated fraction) were separated from other solutes by ice affinity (Kuiper et al. (2003) *Biochem. Biophys. Res. Comm.* 300:645-648). The isolated THFs in the R1, R2 and R3 fractions weighed ~125 µg, ~100 µg and ~60 µg, respectively, and exhibited approximately 3.7±0.3° C. of TH at 5 mg/ml, a value comparable to that of the most active insect antifreeze proteins (Duman (2001) *Annu. Rev. Physiol.* 63:327-357).

THFs (2-5 µg) from each extraction were analyzed by PAGE. The THFs migrated towards the anode on both native and denaturing gels (FIG. 1C), but could not be visualized with Coomassie, silver or SYPRO Ruby protein stains (FIG. 1), even though the detection limits of the three assays are 2 to 3 orders of magnitude lower than the amount of THF applied to the gel (Berggren K et al. (2000) *Electrophoresis* 21:2509-2521). These findings indicate that the isolated THF contained little or no protein. One faint protein band (~80 kDa) was detected in the R1 fraction (FIG. 1), but no corresponding band was observed in R2, indicating that an "ice-active" protein was present in the soluble fraction. Certain non-THF ice-active molecules, such as ice nucleating proteins, may be components of the hemolymph of *U. ceramboides* and may be isolated by ice affinity (Wilson et al. (2006) *Environ. Microbiol.* 8:1816-1824). Furthermore, membrane filtration (30,000 MW cut-off) concentrated the ~80 kDa R1 protein in the retentate, while TH was observed only in the filtrate. Treatment of the isolated THF with Pronase had no effect on TH activity, further supporting the absence of a protein scaffold.

Figure 2:
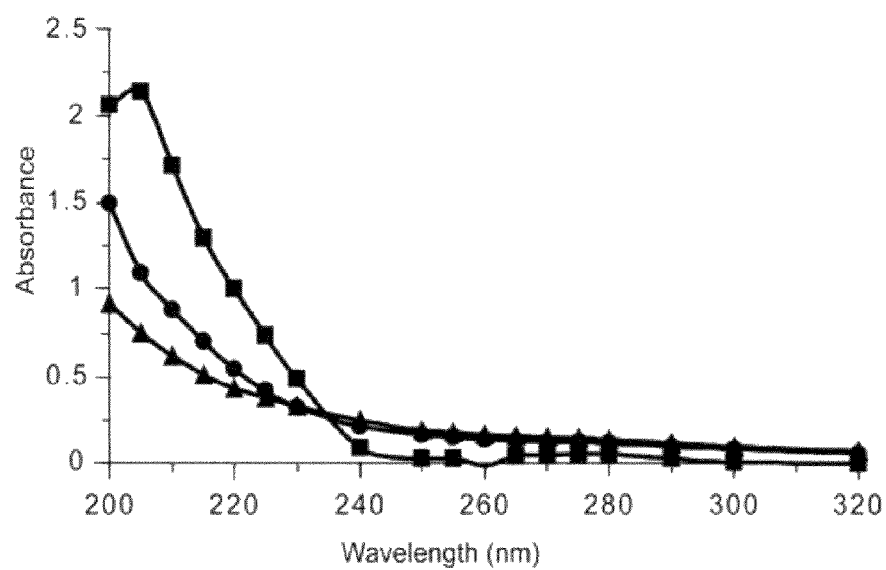
FIG. 2. Ultraviolet absorbance spectra of R1 and R2 AFGL fractions compared to that of BSA. Squares, BSA at 0.12 mg/mL; circles, 1:100 dilution of R2; triangles, 1:100 dilution of R1.
Figure 3:
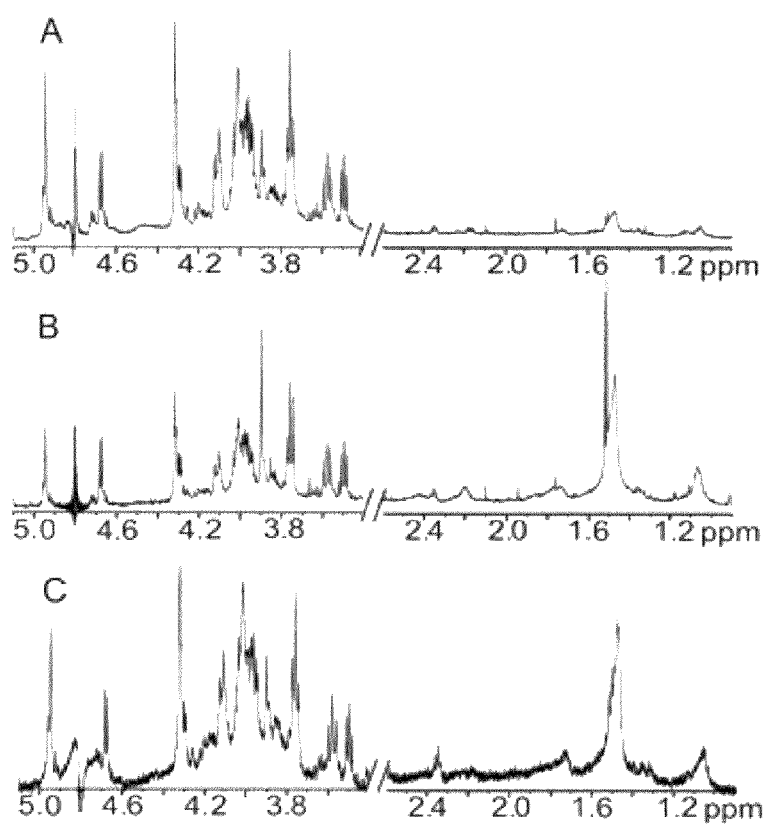
FIG. 3. A comparison of 600 MHz $^1$H NMR. spectra of *U. ceramboides* THFs isolated by ice affinity from three successive extraction buffers. (A) Buffer R1, soluble fraction. (B) Buffer R2, first membrane-associated fraction. (C) Buffer R3, second membrane-associated fraction. Decreasing signal to noise indicates lower THF concentrations.

Ancillary spectrophotometric characterization of the THFs also supports the absence of a significant protein component. Maximal UV absorbance of the THF occurred below 200 nm (FIG. 2); maximal absorbance is expected at 205-220 nm for peptide bonds. In addition, there was no absorbance peak near 280 nm, indicating the absence of aromatic amino acids. $^1$H NMR spectra also lacked any major signals that supported the presence of protein, since all major signals appeared to arise from saccharide and lipid constituents (FIG. 3). Furthermore, $^1$H NMR spectra lacked downfield resonances characteristic of aromatic protons, although a single, low intensity signal at 8.65 ppm was observed in the R1 and R2 fractions (for R3, spectral signal/noise was not sufficient to permit observation of this signal). However, this singlet is not consistent with the presence of aromatic amino acids, inasmuch as aromatic amino acids give rise to multiple aromatic proton signals. Amino acid chromatographic analysis revealed that the ice-purified sample contained 2-3% amino acid by mass, most likely contributed by contaminating proteins/amino acids or a minor protein component in the THF. These proteins/amino acids can be removed by further purification steps.

The THF is Comprised of a Xylp-Manp Core and Optionally a Lipid Component.

Figure 4:
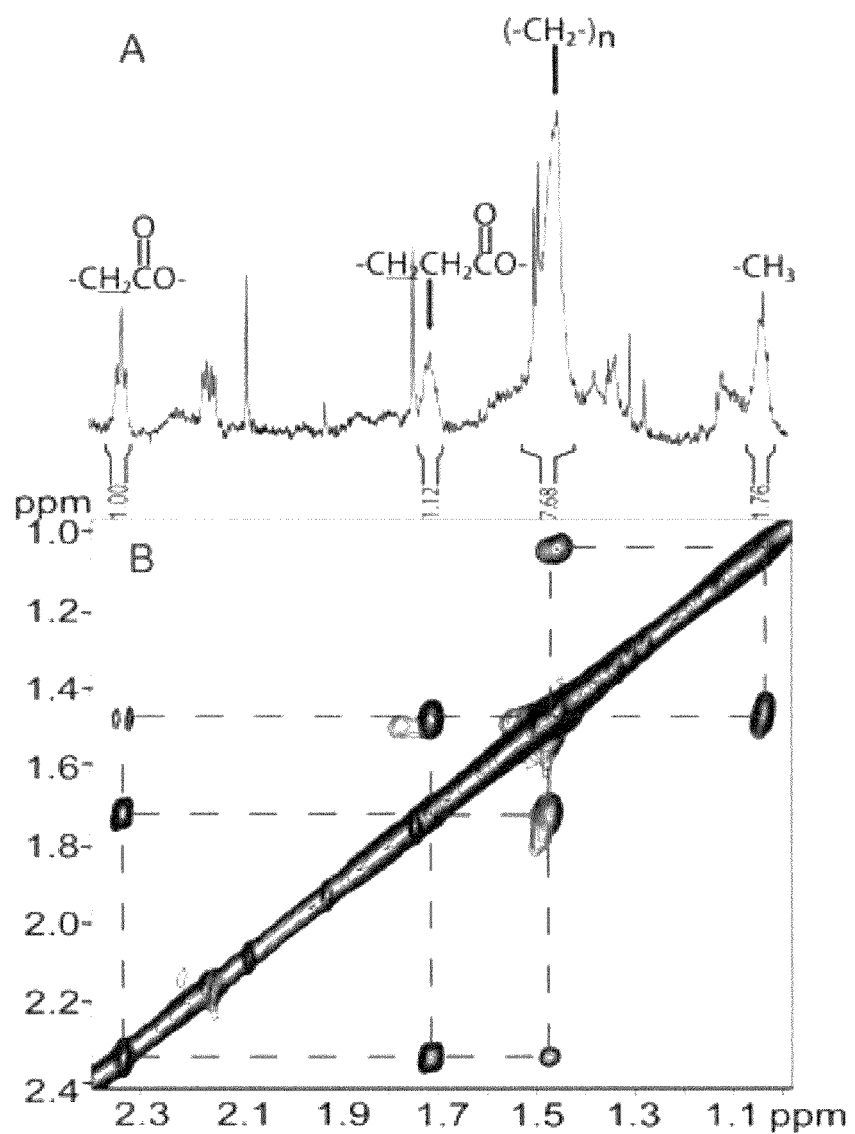
FIG. 4. Partial 800 MHz $^1$H NMR and TOCSY spectra of R1 showing correlations among lipid signals. (A) $^1$H NMR spectrum showing lipid signals that correspond to crosspeaks in (B). Numbers below the bracketed regions indicate relative signal areas. (B) Cross-peaks (connected by dashed lines) in the TOCSY spectrum indicate spin connectivities between $CH_3$ and different types of —$CH_2$-protons in the fatty acid constituent of the R1 THF.

Qualitatively, $^1$H NMR spectra of the R1, R2 and R3 fractions were nearly identical, each containing the same major signals attributable to saccharide and fatty acid components (FIG. 3) based on their characteristic chemical shifts. Inspection of the $^1$H and $^{13}$C chemical shifts, $^1$H-$^1$H scalar couplings ($^3J_{H2,H3}$), signal multiplicities (Table 1), and relative signal areas of the —CH$_2$— and —CH$_3$ signals observed in the $^1$H NMR spectrum of R1 (FIG. 4) indicate the presence of a saturated fatty acid. 2D $^1$H-$^1$H total correlation spectroscopy (TOCSY) data showed that the putative fatty acid signals in R1 arise from a single spin system (FIG. 4). The $^1$H NMR spectrum of R2 contained two additional broad signals, observed at 5.5 ppm (—HC=CH—) and 2.2 ppm (—H$_2$C—HC=CH—CH$_2$—), indicating the presence of unsaturated fatty acid in this sample (Huang and Anderson (1989) *J. Biol. Chem.* 264:18667-18672).

TABLE 1

$^{13}$C and $^1$H chemical shifts (ppm) and $^1$H—$^1$H spin-couplings for lipid signals in R1 compared to those observed for a glycolipid isolated from *Deinococcus radiodurans*.

| | Chemical shifts (ppm)[a] | | | | J-coupling |
|---|---|---|---|---|---|
| | C<u>H</u>$_2$CO | C<u>H</u>$_2$CH$_2$CO | —CH$_{2-n}$ | C<u>H</u>$_3$ | (Hz) |
| Fatty acid-R1 | | | | | $^3J_{H2,H3}$ |
| δ $^{13}$C | — | — | 28.6 | — | 7.5 ± 0.1 |
| δ $^1$H | 2.33 | 1.71 | 1.43-1.52 | 1.04 | |
| multiplicity | triplet | multiplet | multiplet | multiplet | |
| Fatty acid[b] | | | | | $^3J_{H2,H3}$ |
| δ $^{13}$C | — | — | ~29 | — | 7.4 |
| δ $^1$H | 2.33 | 1.62 | 1.1-1.4 | 0.87-0.92 | |
| multiplicity | triplet | multiplet | multiplet | triplet × 3 | |

[a] In $^2$H$_2$O at 40° C., pH 7.5; accurate to ±0.01 ppm. Chemical shifts were referenced to the internal HOD signal (4.800 ppm).
[b] Data from Huang and Anderson (1989) *J. Biol. Chem.* 264:18667-18672.

There were notable quantitative differences between the spectra. $^1$H NMR spectra of the membrane-extracted fractions, R2 and R3, contained considerably more intense lipid signals than did that of the soluble R1 fraction (FIG. 3), indicating a greater fatty acid component in R2 and R3, which indicates that the fatty acid component may anchor the THF to the cell membrane. The lipid may be electrostatically linked or covalently linked to the saccharide constituent.

Figure 5:
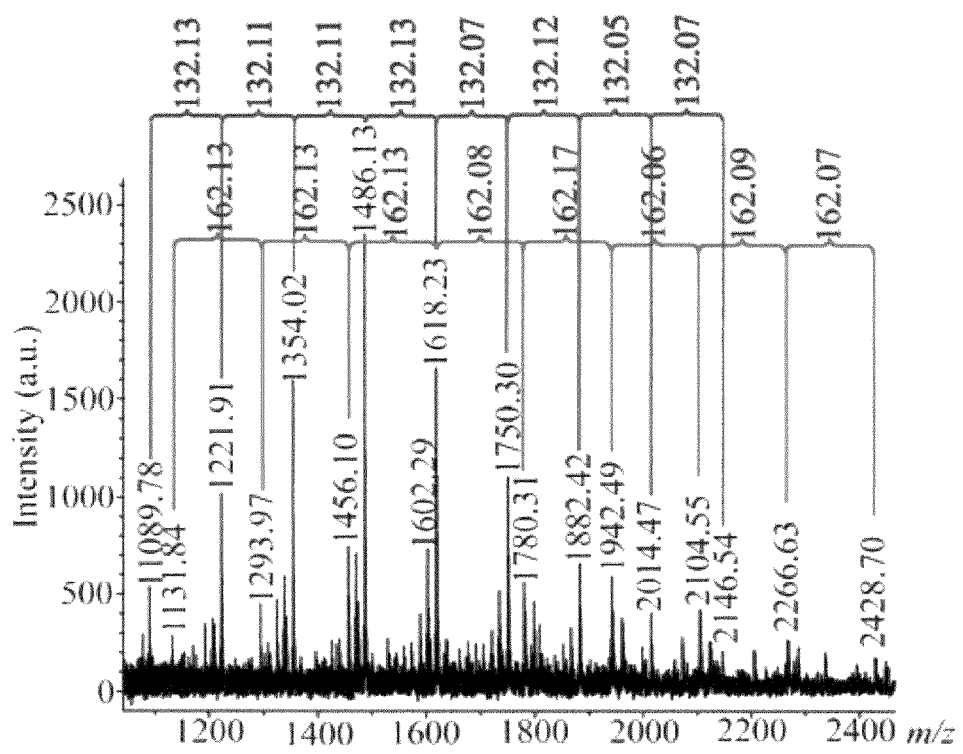
FIG. 5. MALDI-TOF mass spectrum of R1. Lower and upper brackets indicate ions separated by either the mass of an aldohexose (180.06-18.01 (reducing end $H_2O$)=162.05 Da) or aldopentose (150.05-18.01 (reducing end $H_2O$)=132.04 Da), respectively.

Methanolysis of R1 followed by tandem GC/MS analysis of derivatized monosaccharides showed that the two predominant monosaccharides in the R1 sample were mannose (Man) and xylose (Xyl). These results are consistent with the characteristics of the anomeric $^1$H signals observed in the $^1$H NMR spectrum based on signal intensities and splittings (FIG. 3). The ~1.3:1 Man:Xyl molar ratio, determined by integration of the anomeric proton signals, was nearly identical to that determined by GC/MS composition analysis. Data obtained from matrix-assisted laser-desorption ionization (MALDI) mass spectrometry were consistent with a xylomannan structure, given that oligomers that varied by the mass of aldopentose and aldohexose monomers were observed (FIG. 5). The observation that the predominant hexose (Man) and pentose (Xyl) series share a common ion at 1618.23 m/z indicated that Man and Xyl comprise a core repeating structure.

The average molecular weight of the THFs is generally bounded by the results of MALDI (1,000-2,400 Da) and centrifugal filtration experiments (<30 kDa). However, MALDI can substantially underestimate the molecular weight of polysaccharides because oligosaccharides suppress the ionization and desorption of larger saccharides (Garrozzo et al. (1995) *Rapid Commun. Mass Spectrom.* 9: 937-941). Thus, the MALDI data may represent oligomers resulting from the degradation of the THF during storage.

The THFs Contain a β-Mannopyranose-(1→4) β-Xylopyranose Backbone.

Figure 6:
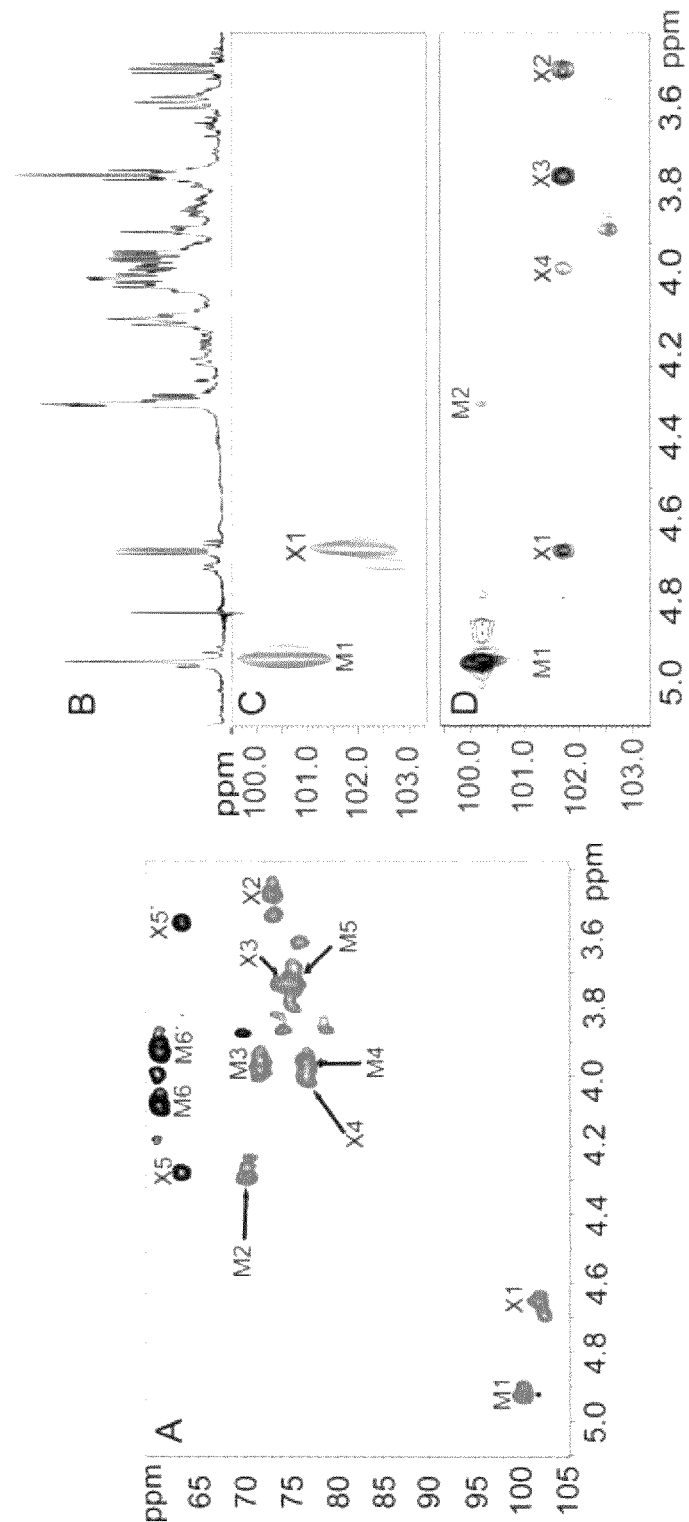
FIG. 6. Partial 2D $^1$H NMR spectra of R1 at 800 MHz. (A) Partial HSQC spectrum showing $^1$H-$^{13}$C correlations for the saccharide $^1$H signals shown in (B). Black contours correlate $^{13}$C and methylene (—$CH_2$—) protons, and red contours correlate $^{13}$C to methine (—CH=) or methyl (—$CH_3$) protons. Crosspeak assignments for the Manp and Xylp constituents are shown as M1-M6' and X1-X5', respectively. (B) Partial 1D $^1$H NMR spectrum showing saccharide signals observed for R1 (C) Expansion of the anomeric signals observed in the HSQC spectrum. (D) Partial HSQC-TOCSY spectrum showing proton signals in (B) that correlate with the anomeric signals observed in (C), allowing identification of most of the ring protons in Xylp, but only H2 in Manp due to the small $^3J_{H1,H2}$ and $^3J_{H2,H3}$ values in Man residues.

The saccharide $^1$H NMR signals for R1 were assigned using a combination of DQF-COSY, TOCSY, HSQC and HSQC-TOCSY 2D NMR methods (FIG. 6). $^1$H and $^{13}$C chemical shift assignments were consistent with those reported previously for Man and Xyl aldopyranosides when chemical shift patterns and signal multiplicities were taken into account (Table 2). The $^1$H chemical shifts of H3 and H4 of Man were nearly identical, however, leading to the possibility that the $^1$H signal assignments, and $^{13}$C assignments derived from HSQC, might be reversed. The implications of this uncertainty are discussed below.

NMR analysis indicated that the Man and Xyl monosaccharide constituents are in the pyranosyl ring form (see preceding paragraph) and both are predominantly in the β-configuration. $^1$H-$^1$H spin-coupling constants involving the anomeric (H1) proton were used to assign anomeric configuration. The value of $^3J_{H1,H2}$ (7.8 Hz) in the xylopyranose (Xylp) constituent was virtually identical to that reported in methyl β-D-xylopyranoside (Podlasek et al. (1995) *J. Am. Chem. Soc.* 117:8635-8644). The anomeric configuration of the Xylp residues was also confirmed with endo β(1→4) xylosidase treatment, which reduced the TH activity of a R1 sample from 0.6±0.1° C. (±SD) to zero within 1 hour of treatment at 22° C.

In authentic methyl D-mannopyranosides, $^3J_{H1,H2}$ for the α and β anomers are 1.8 and 0.9 Hz, respectively. This coupling in the R1 THF was obscured by line broadening (~3 Hz); when resolution enhancement was applied, the Manp H1 signal still appeared nearly symmetric and unsplit, suggesting a $^3J_{H1,H2}$ coupling <1 Hz, indicative of a β-configuration. To gain more information on the Manp anomeric configuration, the one-bond $^1J_{C1,H1}$ coupling was measured, which coupling is very sensitive to anomeric configuration in Manp structures. The observed value of ~160 Hz supported a β-configuration; however, broad signals and relatively poor signal/noise observed in the proton-coupled $^{13}$C NMR spectrum led to uncertainty (±10 Hz) in this measurement, allowing for the possibility that the Manp ring may be in the α-configuration ($^1J_{C1,H1}$ for α-Manp is 171.0 Hz), or there may be a combination of the two configurations. Additional support for the β-Manp configuration was obtained by noting that the chemical shift difference between the H2 and H3 signals (0.32 ppm) in the THF is much closer to the value observed in methyl 13-D-mannopyranoside (0.35 ppm), than in methyl α-D-mannopyranoside (0.17 ppm) (Garrozzo et al. (1995) *Rapid Commun. Mass Spectrom.* 9: 937-941).

Carbon chemical shifts were used to establish the locations of O-glycosidic linkages (see Prohaska et al. (1981) *J. Biol. Chem.* 256:5781-5791). For the β-Manp and β-Xylp constituents, the C4 chemical shifts were displaced downfield by 7-10

TABLE 2

$^{13}$C and $^1$H chemical shifts (ppm) and $^1$H-$^1$H and $^{13}$C-$^1$H spin-couplings for saccharide signals in R1 and standard compounds.

| | Chemical shifts (ppm) | | | | | | |
|---|---|---|---|---|---|---|---|
| | C1 (H1) | C2 (H2) | C3 (H3) | C4 (H4) | C5 (H5, H5') | C6 (H6, H6') | J-coupling (Hz) |
| Man: R1 | 100.2[b] (4.92) | 70.1 (4.30) | 71.6 (3.98) | 76.6[b] (3.96) | 75.1 (3.74) | 60.6 (4.09, 3.93) | $^1J_{C1,H1}$ ~160 |
| methyl α-D-mannopyranoside[c,d] | 101.9 (4.854) | 71.2 (4.024) | 71.8 (3.851) | 68.0 (3.739) | 73.7 (3.70) | 62.1 (3.991, 3.852) | $^1J_{C1,H1}$ 171.0 |
| methyl β-D-mannopyranoside[c,d] | 101.3 (4.658) | 70.6 (4.072) | 73.3 (3.721) | 67.1 (3.625) | 76.6 (3.459) | 61.4 (4.021, 3.825) | $^1J_{C1,H1}$ 159.5 |
| Xyl: R1 | 101.7[b] (4.66) | 72.8 (3.48) | 73.8 (3.73) | 76.6[b] (4.00) | 63.0 (4.28, 3.55) | | $^3J_{H1,H2}$ 7.8 |
| methyl α-D-xylopyranoside[c,d] | 100.6 (4.868) | 72.3 | 74.3 | 70.4 | 62.0 | | $^3J_{H1,H2}$ 3.6 |
| methyl β-D-xylopyranoside[c,d] | 105.1 (4.415) | 74.0 (3.345) | 76.9 (3.533) | 70.4 (3.713) | 66.3 (4.064, 3.419) | | $^3J_{H1,H2}$ 7.8 |

[a]In $^2$H$_2$O at 40° C., pH 7.5; accurate to ± 0.01 ppm. Chemical shifts were referenced to the internal HOD signal (4.800 ppm).
[b]Carbon resonances shifted 7-10 ppm downfield when compared to analogous carbons in the corresponding unsubstituted methyl glycoside, indicating involvement in an O-glycosidic linkage.
[c]Data from Bock and Pedersen (1983) "$^{13}$C NMR Spectroscopy of Monosaccharides", *Adv. Carbohydr. Chem. Biochem.* 41:27-66.
[d]Data from Podlasek et al. (1995) "[$^{13}$C]-enriched methyl aldopyranosides: structural interpretations of $^{13}$C-$^1$H spin-coupling constants and $^1$H chemical shifts", *J. Am. Chem. Soc.* 117:8635-8644.

ppm relative to unsubstituted methyl pyranosides (Table 2), indicating that both saccharides are involved predominantly in β-(1→4) linkages (Scheme 1-1).

Scheme 1-1.

Disaccharide core structure comprising the THF isolated from *U. ceramboides*.

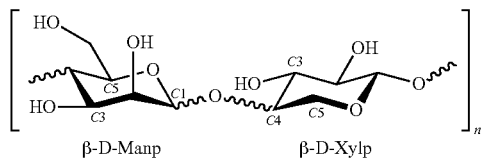

However, other saccharide sequences may also be present and sequences that do strictly alternate between Manp and Xylp may occur. For instance, there may be several tandem Manp residues followed by a series of Xylp residues (block oligomers). In addition, branching may also occur. The above-noted potential variations in the assignment of the Manp H3 and H4 signals allows for the possibility that Man may also be involved in β-(1→6) linkages. Interestingly, treatment of the THF with endo β-(1→4)mannosidase did not affect TH activity.

Although the physiological role of THFs in freeze-tolerance is not completely understood, THFs have been demonstrated to promote cold tolerance. Recrystallization inhibition and/or TH activity increase in response to low temperature in freeze-tolerant insects, other arthropods and plants. For the centipede, *Lithobius forficatus*, experiments showed that THFs (i.e., AFPs) significantly increased cell survivorship under freezing conditions (Tursman and Duman (1995) *J. Exp. Zool.* 272:249-257), although the mechanism has not been definitively elucidated. THFs are potent inhibitors of recrystallization, and thus, one function is the prevention of damage associated with the recrystallization of extracellular ice. The observation that THFs are associated with the cell membrane in the centipede (29), as also appears to be the case for THFs from *U. ceramboides*, indicates that these molecules may prevent the spread of extracellular ice into the cytosol (intracellular freezing is typically thought to be lethal) and/or stabilize the plasma membrane at low temperature.

The study described herein shows that a (lipo)xylomannan isolated from *U. ceramboides* is a highly active THF that is structurally distinct from all known AFPs and AFGPs reported to date. In contrast to known AFGPs, which are comprised of 39% peptide by mass (DeVries et al. (1970) *J. Biol. Chem.* 245:2901-2908), THFs isolated from *U. ceramboides* contain little to no protein. In addition, the β-Manp-(1→4) β-Xylp backbone (Scheme 1-1) is unrelated to the saccharide component of fish AFGPs, which consists of β-D-galactosyl-(1→3)-α-N-acetyl-D-galactosamine disaccharides (Shier et al. (1975) *FEBS Lea.* 54:135-138). This novel xylomannan antifreeze can contribute to freeze tolerance by preventing recrystallization of extracellular ice, preventing intracellular freezing and/or stabilizing cellular membranes at low temperature.

Methods and Materials.

Acclimation.

*U. ceramboides* were cold acclimated in darkness to the following schedule: 0° C., three weeks; −1° C., five days; −2° C., five days; −3° C., 7 days; −4° C., ten days; −5° C., ten days; −6° C., five days; −7° C., five days; and −8° C., two weeks.

THF Extraction and Isolation.

THFs were extracted from beetle whole bodies using a Bio-Rad ReadyPrep sequential extraction kit. The three buffer system permits the solubilization of increasingly hydrophobic biomolecules associated with plasma membrane (Molloy et al. (1998) *Electrophoresis* 19:837-844). Extraction #1 and both washes were retained for ice affinity purification. Extractions #2 and #3 (tributyl phosphine was omitted) and the corresponding washes were dialyzed (3,500 MW cut-off) against distilled water for 24 hours. The osmolality of each sample was adjusted to ~200 mOsm with glycerol prior to ice affinity purification.

THFs selectively adsorb to ice and are incorporated into growing ice crystals, whereas other solutes are excluded. Thus, successive rounds of freezing permit the purification of THFs to homogeneity (Kuiper et al. (2003) *Biochem. Biophys. Res. Comm.* 300:645-648). The extractions and washes were aliquotted into 50 mL centrifuge tubes and placed in an alcohol bath set to −3.6° C. Ice formation was initiated at the bottom of the tube with Fisherbrand spray freeze. After freezing overnight, the bottom 2.5 mm of each tube were excised with a razor blade and the unfrozen portion removed by centrifuging the tube at 2000 rpm for one minute at 4° C. The frozen fraction (>90%) was transferred to a new 50 mL centrifuge tube and thawed. The osmolality was readjusted to ~200 mOsm with glycerol and the sample was subjected to eight additional freeze-thaw cycles. On the ninth and final cycle, no glycerol was added to the sample, but the bath temperature was increased to −1.3° C. to remove residual glycerol from the sample. After the final cycle, the sample was dialyzed against distilled water for 48 hours, lyophilized and reconstituted in 20-50 μL of MilliQ water.

Membrane Filtration.

The R1 fraction was filtered through a Microcon Centrifugal filter device (Millipore, 30,000 MW cut-off) at 5,000 g for ~20 minutes. Prior to application of the sample to the filter cup, the filtration membrane was rinsed twice with distilled water. After the initial filtration, the retentate was rinsed twice, each time with 200 μL of distilled water. All filtrate fractions were consolidated, lyophilized and reconstituted prior to measurement of TH activity and subsequent NMR analysis. The retentate was resuspended in 20 μl, of distilled water to permit both the measurement of TH activity and analysis by polyacrylamide gel electrophoresis.

Thermal Hysteresis Measurements.

TH was measured using a Clifton Nanoliter Osmometer (Clifton Technical Physics) (Walters et al. (2009) *J. Exp. Biol.* 212:305-312).

NMR Spectroscopy.

Lyophilized THF samples (R1 was filtered through 30,000 MWCO filter) were dissolved in 200 μL of $^2H_2O$ containing ~20 mM sodium phosphate buffer, pH 7.5, and placed into a 5 mm symmetrical Shigemi NMR microtube susceptibility-matched to $^2H_2O$. Initial 1D $^1H$ NMR spectra were obtained on a Varian UNITYPlus 600 MHz FTNMR spectrometer. Data acquisition parameters were as follows: 1,000 transients; 3 s recycle time; 313.15 K; −4 to 12 ppm spectral window. A line broadening function (0.2 Hz) was applied to free induction decays prior to Fourier transformation, yielding a final digital resolution of 0.07 Hz/pt. Spectra were referenced internally to the residual HOD signal (4.800 ppm).

Subsequent 1D and 2D spectra were obtained from the R1 sample (prepared as described above) on a Bruker Avance 800 MHz NMR spectrometer equipped with a 5 mm cryoprobe. The data acquisition parameters for 1D $^1$H spectra were as follows: 80 transients; 3 s recycle time; 298.15 K or 313.15 K; spectral width 9615 Hz; digital resolution, 0.29 Hz/pt.

All two-dimensional NMR spectra were acquired in a phase-sensitive mode using the time proportional phase incrementation for quadrature detection in the t1 dimension. TOCSY spectra were collected using isotropic mixing of times of 31 and 80.5 ms at 298.15 K. DFQ-COSY spectra were also collected at 298.15 K. The data size for these spectra were 2048 (t2)×512 (t1). For all 2D spectra, data processing was performed on Bruker Biospin software and phase-shifted sine-squared window functions were applied prior to Fourier transformation. For TOCSY and DFQ-COSY spectra, final matrix sizes were 2048×2048 real points with a final digital resolution of 4.7 Hz/pt in both F1 and F2. HSQC and HSQC-TOCSY spectra were collected at 313.15 K. Data size for HSQC and HSQC-TOCSY spectra were 2048 (t2)× 256 (t1) and spectral widths were 22 kHz in the $^{13}$C dimension and 9,600 Hz in the $^1$H dimension. For the HSQC spectrum, the final matrix size was 2048×1024 real points with a final digital resolution of 10.8 Hz/pt and 4.7 Hz/pt for F1 and F2, respectively. For the HSQC-TOCSY spectrum, the final matrix size was 2048×512 real points with a final digital resolution of 43 Hz/pt and 4.7 Hz/pt for F1 and F2, respectively.

$^{13}$C{$^1$H} NMR spectra were also obtained on the Bruker 800 MHz spectrometer (200 MHz $^{13}$C). The data acquisition parameters were as follows: 32,000 transients; 3 s recycle time; 313.15 K; 48,076 Hz spectral window. A line broadening function (3 Hz) was applied to free induction decays prior to Fourier transformation, yielding a final digital resolution of 0.73 Hz/pt. Conditions for obtaining the $^1$H-coupled $^{13}$C NMR spectrum were identical to those described above, with the exception that broadband $^1$H-decoupling was not employed during data acquisition and 56,000 transients were collected.

Amino Acid Chromatographic Analysis.

Twenty micrograms of isolated THF from *U. ceramboides* and an ice-purified blank (Tris buffer subjected to ice-affinity process) were sent to Texas A&M Protein Chemistry Laboratory for amino acid analysis. Four different samples were run for this assay: the ice-purified THF sample, the ice-purified blank, the assay blank and Human Serum Albumin as a control. Two internal standards norvaline (for primary amino acids) and sarcosine (for secondary amino acids) were added at the beginning of the assay to all samples to control for errors due to sample loss, injection variations and variability in preparing dilutions.

Each sample was mixed with the internal standards, divided into two aliquots and dried in glass tubes in a vacuum concentrator prior to vapor phase hydrolysis by 6N HCl at 150° C. for 1.5 hours under an argon atmosphere. The samples were subsequently reconstituted in 0.4 N Borate Buffer to bring the pH to 10 for optimum derivitization and transferred to the AminoQuant autosampler for automated derivatization and loading. Amino acid analysis was performed using a HP AminoQuant II system. The system consists of an HP 1090 liquid chromatograph with an Hewlett Packard Chemstation equipped with software that controls the LC and collects, analyzes and reports the data.

Sugar Composition Analysis.

Sugar composition analysis was performed at the Complex Carbohydrate Research Center at the University of Georgia by combined gas chromatography/mass spectrometry (GC/MS) of the per-O-trimethylsilyl (TMS) derivatives of the monosaccharide methyl glycosides produced from the sample by acidic methanolysis (Merkle and Poppe (1994) *Methods Enzymol.* 230:1-15; York et al. (1985) *Methods Enzymol.* 118:3-40). Methyl glycosides were prepared from the isolated THF by methanolysis in 1 M HCl in methanol at 80° C. (18-22 hours), followed by re-N-acetylation with pyridine and acetic anhydride in methanol (for detection of amino sugars). Twenty micrograms of inositol were added to the sample as an internal standard. The samples were then per-O-trimethylsilylated by treatment with Tri-Sil (Pierce) at 80° C. (0.5 hours). GC/MS analysis of the TMS methyl glycosides was performed on an HP 6890 GC interfaced to a 5975b MSD, using an All Tech EC-1 fused silica capillary column (30 m×0.25 mm ID).

Enzymatic Hydrolysis Reactions.

For each of the following enzymatic treatments, 1 µL of THF solution (1-4 mg/mL) was diluted 1:1 with Pronase stock solution.

Treatment A (positive control). Pronase stock solution consisted of 2 mg/mL Pronase (a broad spectrum protease) in Tris buffer, pH 7.5, containing 10 mM $CaCl_2$. The reaction mixture was covered with mineral oil and incubated overnight at 37-40° C. A 1:100 dilution of hemolymph from cold acclimatized *Dendroides canadensis*, an AFP-producing beetle, was used as a positive control for the Pronase treatment.

Treatment B. Endo β-(1→4) xylanase stock solution consisted of 2 mg/mL xylanase in 50 mM sodium citrate buffer, pH 5.0. The reaction mixture was held at 22° C. for 1 hour.

Treatment C. Endo β-(1→4) mannanase stock solution consisted of a 1:10 dilution of ammonium sulfate enzyme suspension in 100 mM Mops, pH 7.0. Alternatively, the stock solution was prepared by dialysing the enzyme suspension overnight at 4° C. against 100 mM Mops, pH 7.0. The mixture was covered with mineral oil and incubated overnight at 37° C.

For the negative control in each of these treatments, the enzyme was omitted from the enzyme buffer added to the THF sample. The TH of all samples was measured immediately after addition of the enzyme and again after incubation.

MALDI-TOF Mass Spectrometry.

The R1 sample was analyzed on a Bruker Autoflex III MALDI-TOF/TOF mass spectrometer in the negative polarity/reflector mode (detection range: 0-5000 m/z with deflection up to 500 m/z). A 1-µL quantity of diluted sample (~4 µg/mL) was added to 1 µL of saturated 2,5-dihydroxybenzoic acid in 50/50 (v/v) acetonitrile/water.

Example 2

Thermal Hysteresis-Producing Xylomannan Glycolipid Antifreezes

The presence of large-molecular-mass, thermal hysteresis (TH)-producing antifreezes (e.g., antifreeze proteins) has been reported in numerous and diverse taxa, including representative species of fish, arthropods, plants, fungi, and bacteria. However, relatively few of these antifreeze molecules have been isolated and chemically characterized. A novel non-protein xylomannan glycolipid with TH activity was recently isolated from the freeze-tolerant beetle, *Upis ceramboides* (described above in Example 1; see also Walters et al., *Proc. Natl. Acad. Sci. USA* 2009, 106:210-215 and references cited therein). NMR, sugar composition and enzymatic analyses revealed that a xylomannan was responsible for the observed TH. As described below, the TH-producing xylomannan compounds are shown to be widely distributed in both freeze-tolerant and freeze avoiding organisms across phylogenetically diverse taxa.

Diverse species were screened by subjecting their homogenates to ice-affinity purification. A xylomannan-based TH-producing glycolipid, described in Example 1 above, and related compounds, were discovered, thereby providing a new class of antifreeze glycolipids. The xylomannan-based antifreeze glycolipids were isolated from one plant species, six insect species, and the first frog species shown to produce a large-molecular-mass antifreeze. $^1$H NMR spectra of the ice-purified molecules isolated from these diverse freeze-tolerant and freeze-avoiding organisms were nearly identical, indicating that the chemical structures of the glycolipids are highly similar or the same. Although the exact functions of the antifreeze glycolipids (AFGLs) in these species remain uncertain, it has been determined that the AFGLs play a role in cold tolerance and can be advantageously included in therapeutic, prophylactic, and agricultural compositions as described herein.

Materials and Methods.

Collection Sites/Study Organisms.

Local plants, insects and fish were collected near the University of Notre Dame (South Bend, 1N, USA) from mid-autumn to late winter, to ensure that they were cold hardy. These included three freeze-tolerant species (larvae of the cranefly *Tipula trivittata*, bittersweet nightshade plants *Solanum dulcamara*, and sugar maple *Acer saccharum*), and three freeze-avoiding species, including two species of insects (larvae of the beetles *Dendroides canadensis* and *Ceruchus piceus*) and one species of fish (bluegill sunfish *Lepomis macrochirus*). In order to compare winter and summer acclimatized individuals, *T. trivittata, S. dulcamara* and *C. piceus* were collected during both summer and winter. *Anopheles gambiae* mosquitoes, raised in the laboratory, were used as a negative control because, as a tropical species, *A. gambiae* are not expected to exhibit TH.

Three species of insects: stonefly *Nemoura arctica* nymphs, adult *Upis ceramboides* beetles, and larvae of the beetle *Cucujus clavipes puniceus*, were collected from interior Alaska in late September and were cold acclimated prior to sampling. *N. arctica* nymphs, which are freeze-tolerant, were collected from the headwaters of the Chandalar River in the Brooks Range, AK and acclimated in the laboratory to –8° C. (Walters et al., *J. Exp. Biol.* 2009, 212:305-312). Both *U. ceramboides* (freeze tolerant) and *C. c. puniceus* (freeze-avoiding) were collected near Fairbanks, Ak. and acclimated to –8° C. in a stepwise manner according to Walters et al. (*Proc. Natl. Acad. Sci. USA* 2009, 106:210-215).

Freeze-tolerant frogs, *Rana lessonae* (Voituron et al., Am. J. Physiol. Regul. Integr. Comp. Physiol. 2005, 288: R1563-R1570), were collected from late August to mid-September near Lyon, France. *Rana lessonae* were distinguished from *R. esculenta* and *R. ridibunda* by allozymic differences in lactate dehydrogenase, detected by protein electrophoresis of somatic tissues (finger-tip). The frogs were then cold acclimated at 4° C. in darkness without food for at least 6 weeks before experimentation.

Isolation of TH Factors:

Extraction Procedures.

When assaying for the presence of xylomannan antifreeze, several different purification schemes were used to reduce the presence of protein contaminants. For some species, ice-affinity-based purification of aqueous extracts yielded high purity xylomannan antifreezes. However, aqueous extracts of other organisms were contaminated with large amounts of AFPs and/or ice nucleator proteins. This problem was addressed in most species by extraction with chloroform/methanol, which precipitated contaminating proteins without causing a noticeable loss of the xylomannan. However, for a few species that produce highly soluble AFPs, chloroform/methanol extraction did not fully remove the contaminating proteins. In these situations, a two-step extraction was performed to remove many of the contaminating AFPs. A first aqueous extraction step, which removed most of the highly soluble AFPs, was followed by a chloroform/methanol extraction step and then the sample was treated with Pronase to remove residual AFPs.

Aqueous Extracts.

Aqueous extractions were performed with the BioRad ReadyPrep sequential extraction kit (see Example 1 above), which contains three buffers that solubilize increasingly lipophilic (membrane-associated) molecules. For the first step, organisms/tissues were homogenized with 8 mL of ice-cold 50 mM Tris HCl (pH 7.4) buffer per gram fresh mass. For large scale homogenizations (initial mass >10 g), tissues were homogenized in a blender and subsequently sonicated with a W-385 Sonicator (Heat systems-Ultrasonics, Inc.), using the sonicator horn, for three 30 s intervals at power level six. For small amounts of tissue, samples were minced in 1.5 mL microcentrifuge tubes using dissecting scissors and then sonicated, using the microprobe tip for three 30 sec intervals at power level 3. For both large- and small-scale extractions, the samples were centrifuged at 10,000 g for 20 min to sediment the insoluble fraction, which was extracted with the subsequent buffers. The soluble fraction was removed and purified via ice-affinity purification (description of procedure follows below).

One-Step Chloroform/Methanol Extraction.

Organisms/tissues were homogenized with 8 mL of ice-cold 50 mM Tris HCl, pH 7.4, buffer per gram fresh mass as described above. Plant tissues were flash frozen in liquid nitrogen and processed in the blender immediately prior to the addition of buffer. The homogenate was extracted for 6-8 h at 22° C. with 5 parts chloroform/methanol (2:1) per 1 part Tris buffer used for homogenization. The aqueous fraction was separated from the organic phase after filtration and concentrated to a syrup on a rotary evaporator at 40° C. The syrup was diluted with MilliQ water until the melting point was ~-0.37° C. and subsequently subjected to ice affinity purification.

Two-Step Chloroform/Methanol Extraction.

In contrast to the 1-step chloroform/methanol extraction, samples were processed with an additional extraction step to remove contaminating proteins. In the two-step process, the sample was homogenized in Tris buffer as described above. The cellular debris was subsequently sedimented at 10,000 g for 20 min. After centrifugation, the aqueous soluble fraction was removed and discarded, and the cellular debris was resuspended in the original volume of Tris buffer and extracted with chloroform/methanol as described above. This latter extract was retained for ice-purification.

*Ceruchus piceus* Dissection.

Whole bodies of the stag beetle *C. piceus* larvae were extracted, but to determine if antifreeze molecules were concentrated in tissues that interface with the external environment, larvae were dissected and the tissues extracted separately: one sample contained internal tissues that were readily removed from the body cavity (predominantly fat body), while the other sample contained tissues that interfaced with the external environment, including the gut, epidermal, and all other remaining tissues.

Ice-Affinity Purification.

Nearly all biomolecules are excluded from the ice lattice during freezing and are therefore concentrated in the unfrozen fraction. However, ice-active molecules, such as antifreeze proteins and ice nucleators, which are characterized by their ability to interact with the surface of ice, are incorporated into the ice lattice. Ice-active molecules can, therefore, be separated from all other molecules by multiple freeze-thaw cycles (see Example 1 above; see also Kuiper et al., Biochem. Biophys. Res. Comm. 2003, 300:645-648).

Briefly, the melting point of the sample was adjusted to ~−0.37° C. by adding glycerol prior to freezing at −3.6° C. in a temperature-controlled bath. Ice formation was initiated at the bottom of the 50 mL centrifuge tube using Spray Freeze (Fisherbrand). After at least 6 h at −3.6° C., the sample was removed from the bath and the bottom of the centrifuge tube was excised with a utility knife. The sample was immediately centrifuged at 2000 rpm for 1 min at 4° C. to remove the unfrozen fraction through the hole in the bottom of the tube. The frozen fraction was melted, the melting point was readjusted to −0.37° C., and the sample was refrozen. This process was repeated for 8-10 cycles. On the final cycle, no glycerol was added, and instead the bath temperature was increased to −1.3° C. A dialysis tube was soaked overnight in distilled water and then rinsed extensively to remove any contaminants. Samples were then dialyzed to remove excess glycerol and lyophilized.

Pronase Treatment of Tissue Extracts.

Samples were treated with Pronase to remove contaminating proteins co-isolated by ice affinity and not precipitated in the presence of chloroform/methanol. Extracts were prepared as described above and subjected to two cycles of ice affinity purification prior to Pronase treatment. Pronase was added to a final concentration of 1 mg/mL and the samples were incubated overnight at 23° C. Pronase and degraded proteins were removed by eight additional ice purification cycles.

In preliminary experiments, Pronase was also used in crude homogenates to determine if a protein was responsible for the TH activity of a sample. In this case, tissue extracts or hemolymph samples were treated with Pronase overnight at 37° C. and assayed for changes in TH and/or recrystallization.

NMR Spectroscopy.

The entire lyophilized glycolipid sample was dissolved in 200 µL of $^2H_2O$ containing ~20 mM sodium phosphate buffer pH 7.5 and placed into a 5 mm NMR microtube with a susceptibility matched to $^2H_2O$ (Shigemi, Inc., Allison Park, Pa., USA). $^1H$ NMR spectra were obtained on a Varian UNITY Plus 600 MHz FT-NMR spectrometer. The data acquisition parameters were as follows: 1,000 transients; 3 s recycle time; 40° C.; −4 to 12 ppm spectral window. An exponential line broadening function (0.2 Hz) was applied to the free induction decay prior to Fourier transformation, yielding a final digital resolution of 0.07 Hz/pt. Spectra were internally referenced to the residual water signal, which was set to 4,800 ppm.

Thermal Hysteresis Measurements.

The lyophilized glycolipid was reconstituted in 20-50 µL of 20 mM sodium phosphate buffer, pH 7.5. A small volume of sample (≤0.25 µL) was drawn into a pulled glass micropipette by capillary action and the freezing and melting points were measured using a nanoliter osmometer (Otago Osmometer Ltd, Dunedin, New Zealand). For a more detailed description of this procedure see Walters et al., J. Exp. Biol. 2009, 212:305-312.

Recrystallization Inhibition.

Two microliters of sample were sandwiched between two glass slides placed on the stage of a Linkam BCS 196 cryostage microscope (Linkam Scientific Instruments Ltd., Waterfield, Tadworth, UK). A small amount of mineral oil was placed around the outer edge of the glass slides to prevent desiccation. The sample was frozen by cooling at 40° C./min to −30° C. An initial picture was taken upon warming the sample to −6° C. The sample was then allowed to anneal for one hour before a second picture was taken. The control buffer consisted of 50 mM Tris HCl buffer, pH 7.5, and 1 mg/mL BSA. BSA was added to the control buffer to ensure that "nonspecific" recrystallization inhibition, which is produced by large-molecular-mass molecules, such as peptides, independent of their ability to interact with the surface of ice (Knight et al., Cryobiology 1995, 32:23-34), did not occur. "Nonspecific" recrystallization inhibition can be prevented by the addition of small-molecular-mass solutes. The size of ice crystals in the initial (t=0) and the second (after annealing) pictures was compared to determine if recrystallization had taken place, as indicated by an increase in the size of the crystals with time. Lack of significant growth of the crystals indicates recrystallization inhibition (Knight and Duman, Cryobiology 1986, 23:256-262).

Results.

Ice purified homogenates did not always exhibit TH after ice purification. The presence of thermal hysteresis varied by species and acclimatization. Of the 10 species screened (not including U. ceramboides, which was previously shown to produce an AFGL), seven exhibited more than 0.1° C. of TH activity after ice-purification (Table 2-1). However, TH was only present in winter acclimatized individuals. Tipula trivittata, S. dulcamara and C. piceus collected during the summer did not exhibit TH. Species that exhibited 0.1° C. or less of TH include bluegill sunfish (Lepomis macrochirus 0.05° C.), African malaria mosquito (Anopheles gambiae 0.02° C.), and sugar maple (Acer sacchrum 0.10° C.). A 0.1° C. cutoff TH value was used because the samples had been concentrated several fold, slightly altering the significance of the TH values lower than this cutoff. Samples lacking TH were not analyzed by $^1H$ NMR.

TABLE 2-1

Cold-adapted species that produce xylomannan antifreezes.

| Common name | Species | Initial mass (g) | Extraction Method | TH (° C.) |
|---|---|---|---|---|
| Darkling beetle | Upis ceramboides[t] | 37.57 | 1-step (−Pronase) | 3.7 ± 0.3 |
| Cranefly | Tipula trivittat a[t] | 24.6 | 1-step (+Pronase) | 2.8* |
| Stonefly | Nemoura arctica[t] | 1) 0.5 | 1) aqueous extraction (−Pronase) | 1) 1.3 |
| | | 2) 0.4 | 2) 1-step (−Pronase) | 2) 0.8 ± 0.3 |

TABLE 2-1-continued

Cold-adapted species that produce xylomannan antifreezes.

| Common name | Species | Initial mass (g) | Extraction Method | TH (° C.) |
|---|---|---|---|---|
| Flat bark beetle | Cucujus clavipes puniceus[a] | 0.93 | 2-step (+Pronase) | 1.1 |
| Fire-colored beetle | Dendroides Canadensis[a] | 1.3 | 2-step (+Pronase) | 0.7 |
| Stag beetle | Ceruchus piceus[a] | 1) 3.33 | 1-step (−Pronase) | 1) 0.6 ± 0.1* |
| Bittersweet nightshade | Solanum dulcamara[t] | 1) 8.88 | 1-step (−Pronase) | 1) 3.1 ± 0.4* |
| Frog | Rana lessonae[t] (muscle) | 1.85 | 1) BioRad sequential extractions (−Pronase) | Aqueous 1.4<br>1st membrane-associated 2.0<br>2nd membrane-associated 0.8 |

[t]freeze tolerant organism.
[a]freeze avoiding organism.
The "initial mass" indicates the fresh mass of starting material used for the extraction procedure.
*For these species, both summer and winter acclimatized individuals were checked for TH; individuals collected in summer did not exhibit TH.

Figure 7:
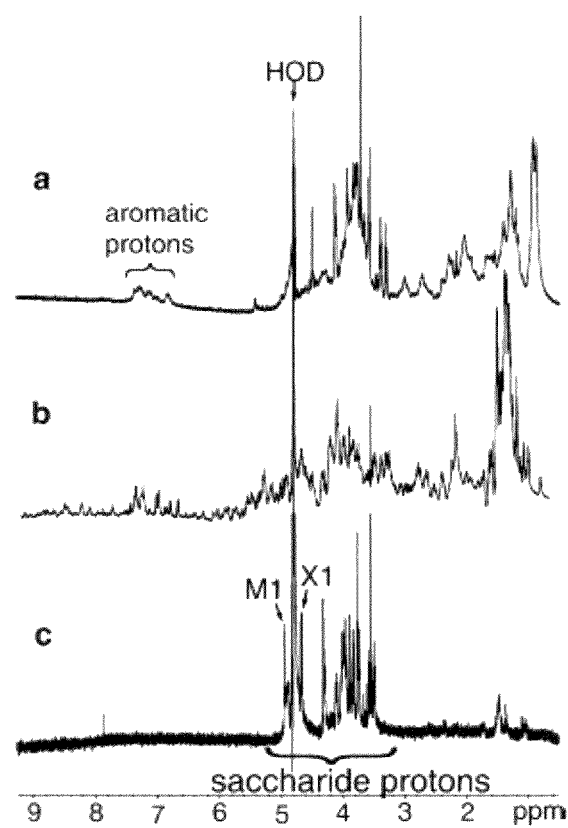
FIG. 7. 600 MHz $^1$H NMR spectra of ice-purified extracts of the insects *Tipula trivittata* (a), *Dendroides canadensis* (b), and *Upis ceramboides* (c). The $^1$H NMR spectra of ice-purified chloroform/methanol extracts of *T. trivittata* (a) and *D. canadensis* (b) contain numerous $^1$H signals arising from protein. There was little to no contaminating protein in the ice-purified aqueous extract of *U. ceramboides* (c). M1 and X1 identify the anomeric protons of mannose and xylose, respectively. For an expanded view of the saccharide protons in (c), see FIG. 9.

The presence of TH did not necessarily indicate the presence of xylomannan antifreeze because contaminating AFPs might have been present. Additionally, ice-nucleating proteins may be co-purified by ice affinity. However, protein-containing samples were readily distinguished from pure glycolipid samples by $^1$H NMR spectroscopy (FIG. 7). In contrast to AFPs, which exhibited numerous overlapping proton signals (FIGS. 7a,b), glycolipids exhibited a limited number of relatively well-defined $^1$H NMR signals (FIG. 7c). In addition, protein-contaminated samples exhibited aromatic proton signals that were absent in pure xylomannan samples (FIG. 7). Even though most proteins were precipitated in the presence of chloroform/methanol, certain AFPs, such as those from Cucujus clavipes puniceus and Dendroides canadensis, were soluble under these conditions. Pronase treatment was used to remove these proteins co-isolated by ice-purification, which otherwise obscured the observation of glycolipid signals (FIG. 7). For D. canadensis, a two-step extraction was necessary to remove contaminating proteins, some of which were resistant to degradation by Pronase.

Pronase treatment of crude samples (homogenates and/or hemolymph) reduced or ablated the TH activity observed in some samples, but did not affect the TH observed in others. For instance, when hemolymph of D. canadensis (known to have multiple isoforms of AFPs) was diluted between 100- and 200-fold, a single Pronase treatment eliminated TH activity (diluted hemolymph was used as a quick positive control for the Pronase treatment; for undiluted hemolymph, TH decreased after Pronase treatment, but the TH measurements took longer and yielded less striking differences between the Pronase-treated and control samples). In contrast, repeated Pronase treatments did not decrease the TH activity in the hemolymph of N. arctica, indicating that the TH was not due to AFPs.

Figure 8:
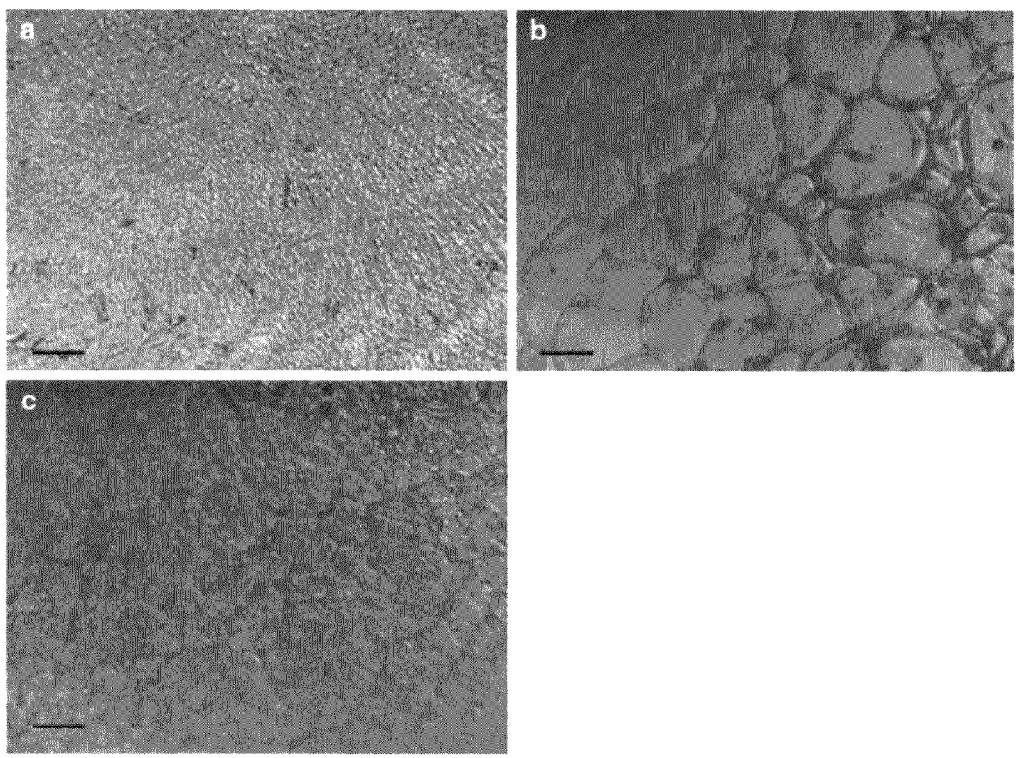
FIG. 8. Comparison of recrystallization of ice crystals in muscle tissue homogenate of the freeze tolerant frog *Rana lessonae* collected in September and acclimated at 4° C. versus ice in a buffer control, consisting of 50 mM tris buffer and 1 mg/mL BSA. a) Representative image of initial time point (the crystal size in both the control buffer and the tissue homogenate was similar); b) Control buffer after annealing; c) *R. lessonae* homogenate after annealing. Samples were frozen by cooling at 40° C./min to −30° C. The initial picture (a) was taken after the sample froze and was warmed to −6° C. The samples (b) and (c) were allowed to anneal at −6° C. for one hour before the second picture was taken. The length of the scale bar represents 100 μm.

Recrystallization experiments demonstrated that ice crystals in the homogenates of tissues obtained from the muscle and skin of the cold-acclimated frog R. lessonae grew more slowly than in the buffer control, indicating that some factor produced recrystallization inhibition (FIG. 8). However, recrystallization inhibition was not observed in blood plasma samples, demonstrating the absence of the antifreeze glycolipid in blood. Only the extracts of skeletal muscle were subjected to ice purification.

The $^1$H NMR spectra of ice-purified glycolipid extracts obtained from the organisms listed in Table 2-1 (FIG. 9) are nearly identical (i.e., they share the same major peaks and shoulders), suggesting a similar core structure of the xylomannan (i.e., both the manno- and xylopyranosyl rings have the β-anomeric configuration) across species. The two major anomeric signals that were observed in all spectra (when collected at 40° C.) occurred at ~4.92 ppm and ~4.66 ppm, which is consistent with the presence of mannose and xylose, respectively. Furthermore, the $^3J_{H1,H2}$ observed for the anomeric signal corresponding to xylose measured ~7.8 Hz across samples, which supports the presence of the β anomer of xylose. For detailed signal assignments and structural data, see Example 1 above. The ratio of the observed peak heights varied somewhat across samples, indicating that the exact composition (e.g., the relative proportions of mannose:xylose:lipid) varies between samples.

Figure 9:
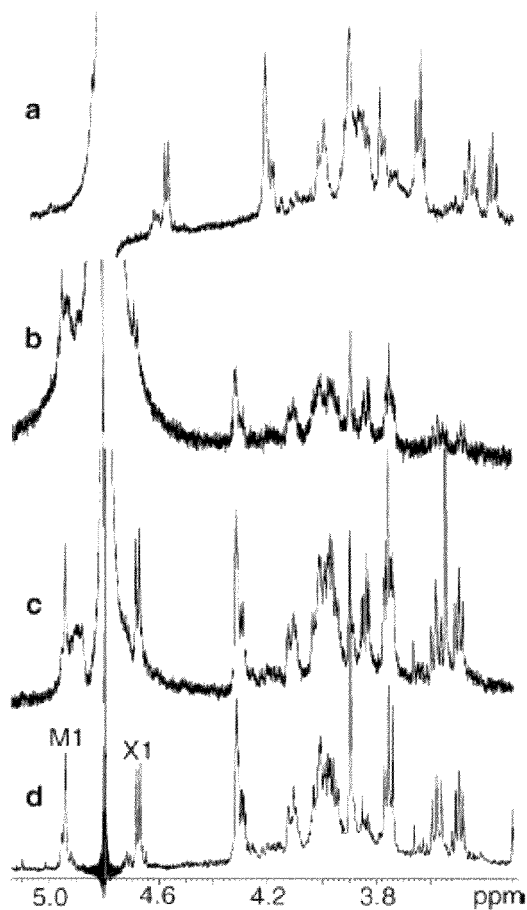
FIG. 9. Alignment of partial 600 MHz $^1$HNMR spectra of ice-purified isolates of *Rana lessonae* (a), a plant *Solanum dulcamara* (b), *Cucujus clavipes* (c), and *Upis ceramboides* (d). The spectrum in panel (a) was acquired at 25° C., while the other spectra shown were acquired at 40° C. The spectrum from *U. ceramboides* is presented as the standard against which the other samples are being compared. M1 and X1 indicate the positions of the anomeric proton signals of mannose and xylose, respectively.

The $^1$H NMR spectrum of the glycolipid isolated from the frog Rana lessonae (FIG. 9a) is shifted relative to the other spectra because it was collected at 25° C. instead of 40° C. A similar temperature dependence was observed for isolates from other species. At 40° C., the mannose H1 signal is well resolved and located downfield of the residual water signal. In contrast, at 25° C., the mannose H1 signal overlaps with the residual water signal. Otherwise, the spectrum from R. lessonae appears virtually identical to the spectra of the isolates from other organisms (FIG. 9).

Figure 10:
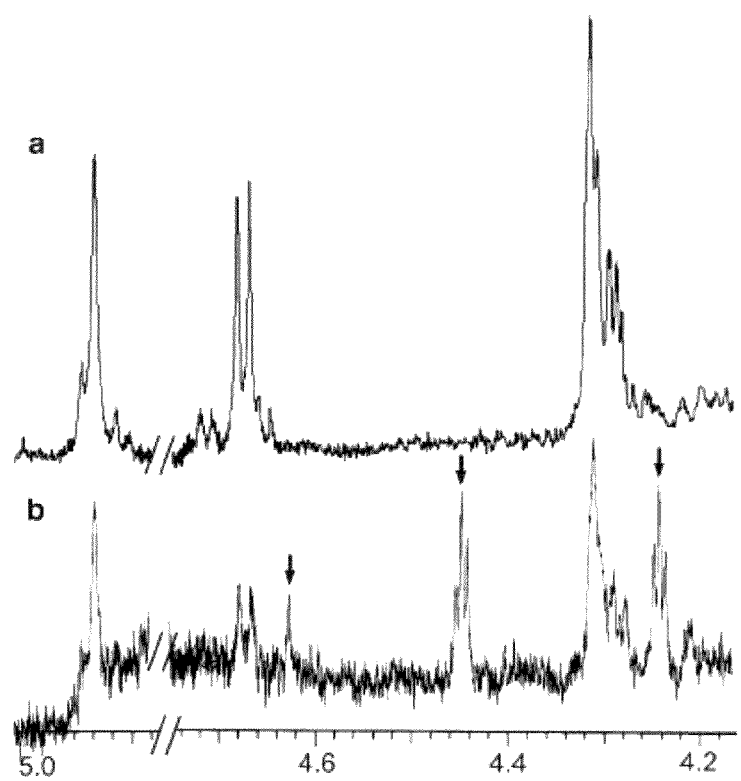
FIG. 10. Alignment of partial $^1$H NMR spectra of ice-purified aqueous extract from two species of freeze tolerant insects: *Upis ceramboides* (a) and *Nemoura arctica* (b). Arrows indicate positions where additional signals were observed in *N. arctica*, but not in *U. ceramboides*.

Notable differences across $^1$H NMR spectra were observed, indicating some structural heterogeneity in the ice purified fractions. The glycolipid isolated from the aqueous fraction of the Alaskan stonefly N. arctica contained $^1$H signals that were not observed in the isolates from other organisms (FIG. 10). These signals suggest the presence of an additional monosaccharide component in the glycolipid structure. The additional signals were observed only in the aqueous extract, not in chloroform/methanol extracts, indicating that the different extraction methods may yield molecules of varying chemical composition.

For the dissection of larvae of the beetle C. piceus, the total initial mass was 1.192 g, of which ~33% of the tissue was removed from the body cavity, while the remaining two-thirds were associated with the gut and epidermis. The gut/epidermal fraction exhibited 0.27° C. of TH, while the fat body tissue exhibited 0.12° C. of TH, suggesting that the level of TH was independent of tissue type and was proportional to the amount of tissue homogenized.

Discussion.

¹H NMR spectra of ice purified THFs from biologically diverse species (plant, insect and amphibian species in Table 2-1) were similar to that observed for the TH-producing xylomannan purified from *U. ceramboides* (Example 1 above), suggesting that the xylomannan structure is evolutionarily conserved. This study is the first to report TH factors of any kind in amphibians, perhaps because the AFGLs exist predominantly in association with the plasma membrane and common procedures do not isolate TH factors adhering to cellular membranes. The association between TH factors and the plasma membrane is supported by the observation that in *R. lessonae* most of the TH was isolated from membrane-associated fractions (R2 and R3) and not the soluble fraction (R1) (Table 2-1). Moreover, recrystallization inhibition in the blood plasma was not observed. In addition, this is the first report of AFGLs in a plant. This study also extends the initial finding of AFGLs in the freeze tolerant beetle *U. ceramboides* to additional freeze tolerant insects (*T. trivittata* and *N. arctica*), and to freeze avoiding species *C. c. puniceus*, *D. canadensis* and *C. piceus*. Two of these insects, *T. trivittata* and *C. piceus*, had been checked previously for the presence of hemolymph thermal hysteresis and no TH, or recrystallization inhibition in *T. trivittata*, was present (Knight and Duman, *Cryobiology* 1986, 23:256-262).

Several lines of evidence indicate that xylomannan-containing AFGLs contribute to cold tolerance. First, a positive correlation exists between cold tolerance and the presence of the antifreeze xylomannan because only cold tolerant species that were winter acclimatized tested positive for AFGLs. AFGLs were not detected in summer acclimatized organisms, nor in species that do not naturally experience (and are not able to survive) subzero temperatures (the fish *L. macrochirus* and the tropical mosquito *A. gambiae*). Second, in previous studies TH measured in the hemolymph of *N. arctica* increased in response to low temperature exposure, and subsequent isolation of the responsible TH factor has shown that a xylomannan-containing glycolipid is responsible for the observed TH. This result is supported by the observation that TH in the hemolymph of *N. arctica* was unaffected by Pronase. Finally, recrystallization inhibition (produced by the same glycolipid) has been reported in the hemolymph of the freeze-tolerant Arctic stonefly *N. arctica* (Walters et al., *J. Exp. Biol.* 2009, 212:305-312), and recrystallization of ice in the extracellular space of freeze tolerant organisms is a potential source of cryoinjury (Tursman and Duman, *J. Exp. Zool.* 1995, 272:249-257).

In addition to the ability of AFGLs to inhibit recrystallization, AFGLs can function to protect freeze-tolerant organisms against cryoinjury by other mechanisms. One important potential function is prevention of the lethal propagation of extracellular ice across the cell membrane into the cytoplasm. Experiments with isolated gut cells from the freeze tolerant centipede, *Lithobius forficatus*, showed that AFPs were able to interact stably with cell membranes, and that when AFPs were associated with the plasma membrane, survivorship of summer isolated cells was comparable to that of winter isolated cells when exposed to freezing conditions. These results indicate that THF's that associate with the cell membrane can prevent the spread of extracellular ice into the cytosol and/or directly stabilize the plasma membrane. Indeed, the TH-producing glycolipids seem strategically positioned to prevent the lethal spread of extracellular ice into the cytosol, since membrane glycolipids are typically displayed asymmetrically on the outer surface of the cell membrane. This orientation would place the presumed ice-binding motif on the cell surface.

Results of additional experiments indicate the ability of antifreeze glycolipids from the bittersweet nightshade, *Solanum dulcamara*, to inhibit intracellular ice formation resulting from ice propagation across the cell membrane. Protoplasts (cells with the cell walls removed) of frost sensitive summer geranium plants were placed on a slide in a cryomicroscope, and held at −1° C. until the temperature was equilibrated. The bathing medium was then frozen by seeding with an ice crystal, and the temperature lowered slowly. This set-up permited the identification of the temperature of cytoplasmic freezing of the cells, as the cells immediately turn opaque (dark) upon freezing. Control cells without the addition of *S. dulcamara* AFGL froze at a median temperature of −4° C. (range of −1.5 to −4.0° C.). However, addition of AFGL (at a very low concentration) to the cells resulted in lowering the median freezing temperature of the protoplasts to below −20° C. The ability of AFGLs to prevent intracellular freezing therefore represents an important physiological adaptation because most freeze tolerant organisms do not survive intracellular ice.

Membrane stabilization at low temperature by the AFGL is also plausible because other TH factors, including fish AFGPs and fish type I AFPs, are known to prevent membrane injury associated with low temperature exposure. Although not all TH factors possess this property, AFGLs are candidates for low temperature membrane stabilization because modulation of the glycolipid composition of the plasma membrane is known to change the physico-chemical properties of the membrane, allowing for seasonal and/or evolutionary thermal adaptation. Another function of the relatively small amount of soluble AFGLs located in the hemolymph can be to slow the growth of extracellular ice and thereby reduce the rate of flux of water and solutes across the cell membrane. Because none of these potential functions are mutually exclusive, AFGLs may have multiple functions in freeze tolerant species.

The function of TH-producing AFGLs in the freeze avoiding organisms identified in this study, especially those known to produce highly active AFPs (*D. canadensis* and *C. c. puniceus*), is less apparent. The observation that AFPs do not all interact with ice in the same manner indicates that AFGLs could complement the functions of AFPs, perhaps contributing to the ability of *C. c. puniceus* to cool below −100° C. without freezing (Sformo et al. *J. Exp. Biol.* 2010, 213:502-509).

This study shows that a class of antifreeze xylomannan glycolipids is widely distributed among diverse taxa, including plants, insects, and amphibians. The observation that TH-producing glycolipids are associated with diverse cold tolerant species as described above, and that TH increases acutely with cold exposure in *N. arctica*, which only produce AFGLs, indicates that TH-producing glycolipids promote cold tolerance. Additional techniques and discussion are described by Walters, *Large Molecular Weight Antifreezes and Related Adaptations in Freeze-Tolerant Alaskan Insects*, Ph.D. Dissertation, University of Notre Dame library, Notre Dame, 1N, July 2009.

Example 3

Frostbite Prevention Formulations

The antifreeze glycolipid compositions (AFGLs) described herein can be used for a variety of therapeutic and cosmetic applications. A major use of the compositions involves the formulating the glycolipid composition into a topical formulation for application to human skin. Because of the lipophilicity of the AFGL compounds and compositions, the AFGLs can penetrate skin, thereby reducing the risk of ice nucleation and protecting the tissue's cells if ice formation does occur. Such application can increase the resistance of human skin to frostbite, for example, at temperatures near or below 32° F., and can minimize the resulting damage if cellular freezing does occur.

In addition to the AFGL component, the topical formulation can also include antifreeze proteins (AFPs), inhibitors of apoptosis or reperfusion injury, and cryoprotectants such as glycerol, dimethylsulfoxide (DMSO) and/or low molecular weight sugars. The topical formulation can be prepared as a cream, lotion, ointment, gel, solution, aerosol or similar formulation. The formulation can include a variety of optional additives, including wetting agents, fragrances, and/or preservatives. The formulation can be applied by hand, by spraying, or the formulation can be used in conjunction with an occlusive backing, such as in an adhesive patch. The formulation should be sufficiently viscous to remain on the skin for an extended period of time. In addition to the barrier function of the topical carrier, the antifreeze glycolipid in the formulation can reduce the occurrence of frostbite due to its thermal hysteresis properties.

Example 4

Fat Removal Formulations

The antifreeze glycolipid compositions described herein can be formulated for topical applications and used in conjunction with fat reduction techniques in humans. Such fat reduction techniques include the reduction of subcutaneous fat by non-invasive cooling of the skin, relying on the greater cold sensitivity of fat cells compared to the overlying epidermal cells in the treated area. The treatment is currently limited by damage to these epidermal cells. Consequently the effectiveness of the procedure can be increased by topically applying a formulation that includes an effective amount of a glycolipid composition described herein. The topical treatment protects the epidermal cells while allowing the lowered temperature to reach the fat cells, causing them to be cleared from the treated area over time, thereby reducing the amount of fat cells in the treated area. The application of the topical glycolipid composition can allow for increased fat reduction compared to the procedure carried out in the absence of the topically applied glycolipid formulation.

While current fat reduction techniques employ topical compositions to reduce the occurrence of frostbite, formulations that include the glycolipid compositions described herein can enable the use of cooler temperatures for longer periods of time because the antifreeze glycolipids act as cellular protectants due to their thermal hysteresis properties. Non-invasive fat reduction techniques are described by, for example, U.S. Patent Publication Nos. 2011/0046616 (Manstein), 2011/0046615 (Manstein), and 2007/0010861 (Anderson et al.), the disclosures of which are incorporated herein by reference.

Example 5

Synthetic Preparation of Xylomannan Antifreeze Glycolipids

The chemical structures of AFGLs that exhibit thermal hysteresis properties contain a repeating [β-D-Manp-(1→4)-β-D-Xylp-(1→4)]$_n$ core structure that, in some cases, is appended with a lipid (fatty acid) constituent. The saccharide backbone can be strictly linear or can contain one or more branch points. The precise mode of attachment of the lipid to the saccharide backbone can vary. In some embodiments, the glycolipids contain lipids attached to the reducing end of the molecule, involving the hydroxyl group on the anomeric carbon.

While the covalent structure of TH-active AFGL can vary, the rationale design of a synthetic analog, such as structure 10 shown in FIG. 11, can be prepared using standard synthetic techniques. Structure 10 is a linear hexasaccharide containing three Man-Xyl repeating disaccharide units and a long-chain alkyl group (e.g., ($C_8$-$C_{24}$)alkyl group, such as a $C_{16}$ alkyl chain) attached glycosidically at the reducing end of the molecule. FIG. 11 illustrates a suitable chemical synthesis route to prepare this hexasaccharide compound. In other embodiments, the alkyl group can be replaced with a fatty acid moiety (e.g., a ($C_8$-$C_{24}$)alkanoyl group, such as a $C_{16}$ acyl group).

Disaccharide 3 is a known β-Gal-(1→4)-β-XylOAlkyl derivative that is central to the route. Structure 3 can be converted to disaccharide 6 by a CsOAc-catalyzed double-inversion at C2 and C4 of the Gal residue, thus converting it to β-Man. This strategy allows installation of the β-Man linkage into disaccharide building block 6 without having to attempt this linkage directly from an activated Man donor, which can be difficult to achieve with high stereoselectivity. Structure 6 serves as the acceptor in a chemical glycosylation reaction involving 7 as the donor. Structure 7 can be prepared by a route similar to that used to prepare compound 6. This glycosylation reaction yields tetrasaccharide 8, which can be subsequently extended to hexasaccharide 9 by a second glycosylation reaction, again with 7 serving as the donor. Product 9 is then deprotected to give crude 10, which can be purified chromatographically or by other suitable techniques.

By varying the number of glycosylation reactions using 7 as the donor, oligosaccharides of different chain lengths can be obtained. The repetitive feature of this synthetic strategy thus allows multiple analogs to be accessed with minimal effort. The route also involves the formation of multiple β(1→4) linkages between Xyl and Man to build the oligosaccharide from disaccharide precursors, not between Man and Xyl; as mentioned above, the latter linkages are more difficult to achieve with high stereoselectivity. Other routes to the same or similar synthetic AFGL can be employed, and the route illustrated in FIG. 11 represents only one variation. Other routes maybe followed by those of skill in the art to prepare the various xylomannan antifreeze glycolipids described herein. For example, the synthesis allows for the systematic incorporation sugars other than Xyl and Man into the structure, to provide xylomannan compounds that include various other sugar groups.

Example 6

Pharmaceutical Dosage Forms

The following formulations illustrate representative pharmaceutical or cosmetic topical preparations that may be used for the therapeutic or prophylactic administration of an antifreeze composition described herein, where the antifreeze xylomannan composition is hereinafter referred to as 'Composition X':

| (i) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

| (ii) Topical Gel 1 | wt. % |
|---|---|
| 'Composition X' | 5% |
| Carbomer 934 | 1.25% |
| Triethanolamine (pH adjustment to 5-7) | q.s. |
| Methyl paraben | 0.2% |
| Purified water | q.s. to 100 g |

| (iii) Topical Gel 2 | wt. % |
|---|---|
| 'Composition X' | 5% |
| Methylcellulose | 2% |
| Methyl paraben | 0.2% |
| Propyl paraben | 0.02% |
| Purified water | q.s. to 100 g |

| (iv) Topical Ointment | wt. % |
|---|---|
| 'Composition X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (v) Topical Cream 1 | wt. % |
|---|---|
| 'Composition X' | 5% |
| White bees wax | 10% |
| Liquid paraffin | 30% |
| Benzyl alcohol | 5% |
| Purified water | q.s. to 100 g |

| (vi) Topical Cream 2 | wt. % |
|---|---|
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

| (vii) Topical Solution | wt. % |
|---|---|
| 'Composition X' | 5% |
| Glycerol | 25% |
| Dimethyl sulfoxide | 1-3% |
| Trehalose | 2% |
| Silwet L-77 Organosilicone | 1% |
| Methyl paraben | 0.2% |
| Purified water | q.s. to 100 g |

These formulations may be prepared by conventional procedures well known in the pharmaceutical or cosmetic arts. It will be appreciated that the above compositions may be varied according to well-known pharmaceutical techniques to accommodate differing amounts and types of active ingredient 'Composition X'. Aerosol formulation (i) may be used in conjunction with various standard aerosol dispensers. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An antifreeze glycolipid composition comprising an isolated polysaccharide moiety of Formula I:

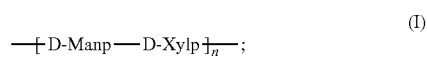

(I)

wherein D-Manp represents a D-mannopyranose moiety, D-Xylp represents a D-xylopyranose moiety, and n is about 5 to about 70;
and one or more lipid moieties covalently linked to the polysaccharide moiety of Formula I or electrostatically associated with the polysaccharide moiety of Formula I.

2. The antifreeze glycolipid composition of claim 1 wherein the mannopyranose and xylopyranose moieties of Formula (I) are linked via beta-linkages.

3. The antifreeze glycolipid composition of claim 1 wherein the mannopyranose and xylopyranose moieties of Formula (I) are linked via β(1→4) linkages.

4. The antifreeze glycolipid composition of claim 1 wherein the polysaccharide moiety of Formula I is linked to one or more blocks of repeating mannopyranose moieties, xylopyranose moieties, or both.

5. The antifreeze glycolipid composition of claim 1 wherein the ratio of mannopyranose moieties to xylopyranose moieties is about 40:60 to about 60:40.

6. The antifreeze glycolipid composition of claim 1 wherein the mass of the mannopyranose moieties and xylopyranose moieties comprise about 90% to about 98% of the glycolipid composition.

7. The antifreeze glycolipid composition of claim 1 wherein the polysaccharide moiety of Formula I comprises a glycolipid moiety of Formula II:

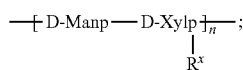   (II)

a glycolipid of Formula III:

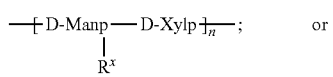   (III)   or a glycolipid of Formula IV:

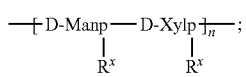   (IV)

wherein each $R^x$ is independently H or a lipophilic moiety $R^L$ covalently bonded to a saccharide moiety of the formula;

each mannopyranose and xylopyranose is substituted with one to three $R^x$ groups, at least one $R^x$ is $R^L$; and $R^L$ is a fatty acid, a mono-, di-, or tri-glyceride, a sterol, or a phospholipid.

8. The antifreeze glycolipid composition of claim 7 wherein the polysaccharide moiety of Formula I comprises a glycolipid moiety of Formula VI:

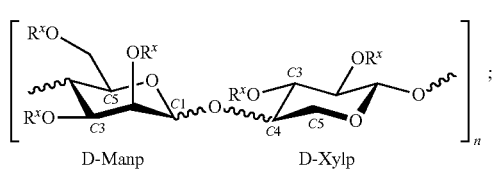   (VI)

wherein each $R^x$ is independently be H or a lipophilic moiety $R^L$, wherein at least one $R^x$ is $R^L$.

9. The antifreeze glycolipid composition of claim 1 wherein the polysaccharide moiety of Formula I comprises a polysaccharide moiety of Formula VII:

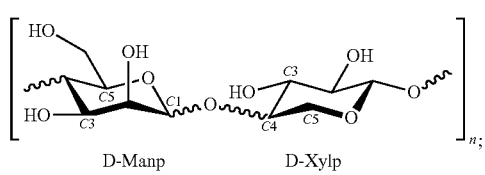   (VII)

where a lipid moiety is electrostatically associated to one or more of the oxygen atoms of the saccharide of Formula VII, and the lipid moiety is an alkyl chain, a fatty acid, a mono-, di-, or tri-glyceride, a sterol, or a phospholipid.

10. The antifreeze glycolipid composition of claim 7 wherein one or more of the lipophilic moieties $R^L$ is a fatty acid, a mono-, di-, or tri-glyceride, a sterol, or a phospholipid.

11. The antifreeze glycolipid composition of claim 7 wherein one or more of the lipophilic moieties $R^L$ is a fatty acid moiety $R^1$ of the formula —C(=O)R wherein R is a straight chain or branched $(C_8-C_{30})$alkyl group.

12. The antifreeze glycolipid composition of claim 7 wherein one or more of the lipophilic moieties $R^L$ is a fatty acid moiety $R^1$ of the formula —C(=O)R wherein R is a straight chain or branched $(C_8-C_{30})$alkyl group wherein the alkyl is optionally unsaturated, optionally epoxidized, optionally substituted with one or more hydroxyl groups, or a combination thereof.

13. The antifreeze glycolipid composition of claim 7 wherein one or more of the lipophilic moieties $R^L$ is a fatty acid moiety $R^1$ wherein $R^1$ is the residue of lauric acid (dodecanoic acid), myristic acid (tetradecanoic acid), palmitic acid (hexadecanoic acid), steric acid (octadecanoic acid), arachidic acid (eicosanoic acid), lignoceric acid (tetracosanoic acid), palmitoleic acid, oleic acid, linoleic acid, linolenic acid, arachidonic acid, or combinations thereof.

14. The antifreeze glycolipid composition of claim 7 wherein one or more of the lipophilic moieties $R^L$ is a glyceride moiety having fatty acid substituents.

15. The antifreeze glycolipid composition of claim 7 wherein one or more of the lipophilic moieties $R^L$ is $R^2$ where $R^2$ is a moiety of Formula VIII:

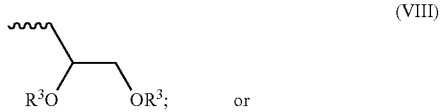   (VIII)   or or a moiety of Formula IX:

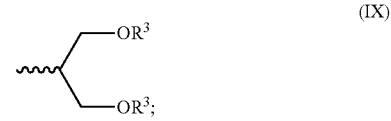   (IX)

wherein each $R^3$ is independently H, R, or $R^1$, each R is independently a straight chain or branched $(C_8-C_{30})$alkyl group, and each $R^1$ is independently a moiety of the formula —C(=O)R.

16. The antifreeze glycolipid composition of claim 7 wherein one or more of the lipophilic moieties $R^L$ is a moiety of Formula X:

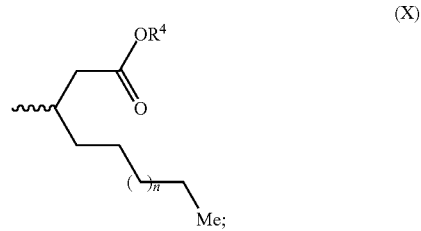   (X)

wherein each $R^4$ is independently H, $(C_1-C_7)$alkyl, R, or $R^1$, each R is independently a straight chain or branched $(C_8-C_{30})$ alkyl group, and each $R^1$ is independently a moiety of the formula —C(=O)R.

17. The antifreeze glycolipid composition of claim 7 wherein one or more of the lipophilic moieties $R^L$ is a moiety of Formula XI:

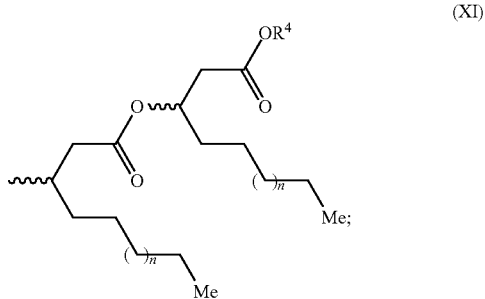

wherein each $R^4$ is independently H, $(C_1-C_7)$alkyl, R, or $R^1$, each R is independently a straight chain or branched $(C_8-C_{30})$ alkyl group, and each $R^1$ is independently a moiety of the formula —C(=O)R.

18. The antifreeze glycolipid composition of claim 7 wherein one or more of the lipophilic moieties $R^L$ is a moiety of Formula XII:

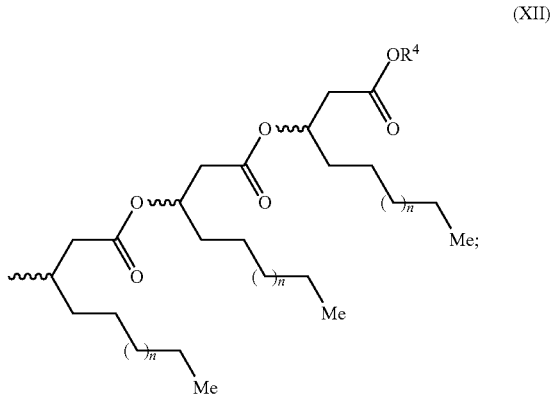

wherein each $R^4$ is independently H, $(C_1-C_7)$alkyl, R, or $R^1$, each R is independently a straight chain or branched $(C_8-C_{30})$ alkyl group, and each $R^1$ is independently a moiety of the formula —C(=O)R.

19. The antifreeze glycolipid composition of claim 7 wherein the lipid moiety or lipophilic moiety $R^L$ is covalently bonded through an oxygen atom at C2, C3, or C6 of a mannopyranose moiety, at C2 or C3 of a xylopyranose moiety, or a combination thereof.

20. The antifreeze glycolipid composition of claim 1 wherein the composition comprises less than 5 wt. % of amino acids.

21. The antifreeze glycolipid composition of claim 1 wherein the composition provides more than 2° C. of thermal hysteresis at a concentration of 5 mg/mL.

22. The antifreeze glycolipid composition of claim 1 wherein the average molecular weight of the polysaccharides that include the moiety of Formula I in the composition is about 1.6 kDa to about 20 kDa.

23. A composition comprising the glycolipid composition of claim 1 and a pharmaceutically, cosmetically, or agriculturally acceptable carrier.

24. An antifreeze glycolipid composition comprising an isolated polysaccharide moiety of Formula I:

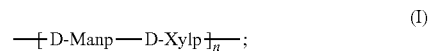

wherein D-Manp represents a D-mannopyranose moiety, D-Xylp represents a D-xylopyranose moiety, and n is about 5 to about 70;

and one or more lipid moieties covalently linked to the polysaccharide moiety of Formula I or electrostatically associated with the polysaccharide moiety of Formula I;

wherein the mannopyranose and xylopyranose moieties of Formula (I) are linked via beta-linkages; and the mass of the mannopyranose moieties and xylopyranose moieties comprise about 90% to about 98% of the glycolipid composition.

25. The antifreeze glycolipid composition of claim 24 wherein the composition comprises less than 5 wt. % of amino acids.

26. A composition comprising the glycolipid composition of claim 24 and a pharmaceutically, cosmetically, or agriculturally acceptable carrier.

* * * * *

UNITED STATES PATENT AND TRADEMARK OFFICE
CERTIFICATE OF CORRECTION

PATENT NO.        : 8,604,002 B1
APPLICATION NO.   : 13/135065
DATED             : December 10, 2013
INVENTOR(S)       : Kent Walters et al.

It is certified that error appears in the above-identified patent and that said Letters Patent is hereby corrected as shown below:

Title Page, please replace Title Page with new Title Page. (attached)

In the Drawings

Figure 11:
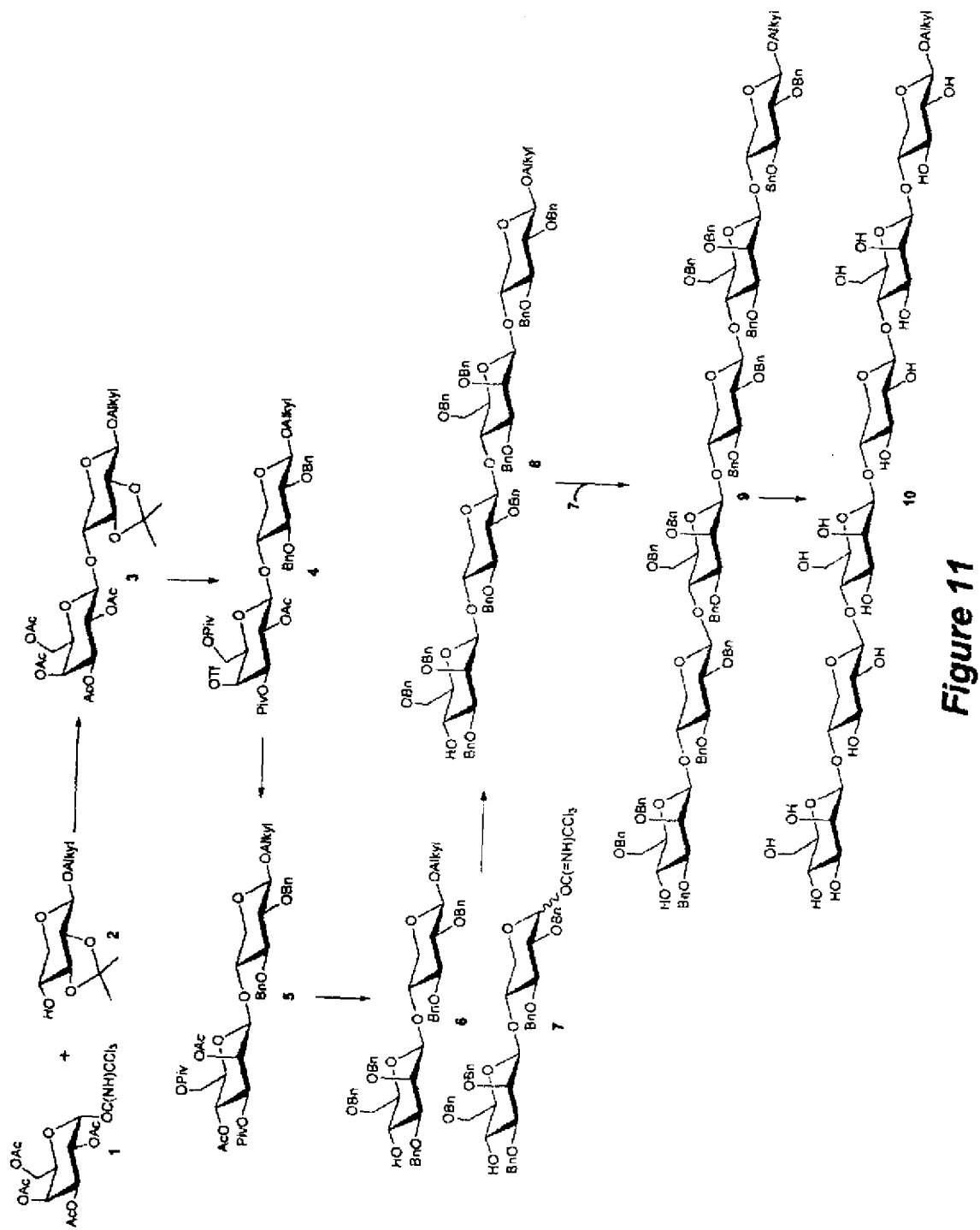
FIG. 11. A scheme illustrating a synthetic route for the preparation of xylomannan glycolipids, according to one embodiment.

After Figure 10, Tenth Sheet of Drawings and before Column 1, line 1, please insert Figure 11 (attached)

First Sheet of Drawings, Line 1, please replace --Sheet 1 of 10-- with --Sheet 1 of 11--

Second Sheet of Drawings, Line 1, please replace --Sheet 2 of 10-- with --Sheet 2 of 11--

Third Sheet of Drawings, Line 1, please replace --Sheet 3 of 10-- with --Sheet 3 of 11--

Fourth Sheet of Drawings, Line 1, please replace --Sheet 4 of 10-- with --Sheet 4 of 11--

Fifth Sheet of Drawings, Line 1, please replace --Sheet 5 of 10-- with --Sheet 5 of 11--

Sixth Sheet of Drawings, Line 1, please replace --Sheet 6 of 10-- with --Sheet 6 of 11--

Seventh Sheet, of Drawings, Line 1, please replace --Sheet 7 of 10-- with --Sheet 7 of 11--

Eighth Sheet of Drawings, Line 1, please replace --Sheet 8 of 10-- with --Sheet 8 of 11--

Ninth Sheet of Drawings, Line 1, please replace --Sheet 9 of 10-- with --Sheet 9 of 11--

Tenth Sheet of Drawings, Line 1, please replace --Sheet 10 of 10-- with --Sheet 10 of 11--

Signed and Sealed this
Seventeenth Day of June, 2014

Michelle K. Lee
*Deputy Director of the United States Patent and Trademark Office*

(12) United States Patent
Walters et al.

(10) Patent No.: US 8,604,002 B1
(45) Date of Patent: Dec. 10, 2013

(54) SACCHARIDE ANTIFREEZE COMPOSITIONS

(75) Inventors: Kent Walters, Notre Dame, IN (US); John G. Duman, Niles, MI (US); Anthony S. Serianni, Notre Dame, IN (US)

(73) Assignee: University of Notre Dame Du Lac, Notre Dame, IN (US)

( * ) Notice: Subject to any disclaimer, the term of this patent is extended or adjusted under 35 U.S.C. 154(b) by 18 days.

(21) Appl. No.: 13/135,065

(22) Filed: Jun. 23, 2011

Related U.S. Application Data

(60) Provisional application No. 61/398,276, filed on Jun. 23, 2010.

(51) Int. Cl.
    *A61K 31/739* (2006.01)
    *C08B 37/00* (2006.01)
    *C09K 3/18* (2006.01)

(52) U.S. Cl.
    USPC .......................... 514/54; 536/123.1; 106/13

(58) Field of Classification Search
    USPC ............... 514/54; 536/123.1; 435/11; 106/13
    See application file for complete search history.

(56) References Cited

U.S. PATENT DOCUMENTS

| | | | | |
|---|---|---|---|---|
| 4,448,702 A | * | 5/1984 | Kaes | ................... 252/70 |
| 5,627,051 A | | 5/1997 | Duman | |
| 5,633,451 A | | 5/1997 | Duman | |
| 2007/0010861 A1 | | 1/2007 | Anderson et al. | |
| 2008/0317704 A1 | | 12/2008 | Obata et al. | |
| 2010/0068692 A1 | | 3/2010 | Ben et al. | |
| 2011/0046615 A1 | | 2/2011 | Manstein | |
| 2011/0046616 A1 | | 2/2011 | Manstein | |

OTHER PUBLICATIONS

Walters et al, Proceedings of the National Academy of Sciences, Dec. 1, 2009, 106(48), pp. 20210-20215.*
Abdel-Mawgoud et al., Rhamnolipids: diversity of structures, microbial origins and roles, Appl Microbiol Biotechnol (Mar. 2010) 86:1323-1336.
Walters et al., A nonprotein thermal hysteresis-producing xylomannan antifreeze in the freeze-tolerant Alaskan beetle *Upis ceramboides*, PNAS, Dec. 2009, vol. 106 No. 48, pp. 20210-20215.
Walters, Large Molecular Weight Antifreezes and Related Adaptations in Freeze-Tolerant Alaskan Insects, Ph.D. Dissertation, University of Notre Dame library, Notre Dame, IN, Jul. 2009, 139 pgs.

* cited by examiner

*Primary Examiner* — Shaojia Anna Jiang
*Assistant Examiner* — Ganapathy Krishnan
(74) *Attorney, Agent, or Firm* — Billion & Armitage

(57) ABSTRACT

The invention provides an antifreeze glycolipid compounds and composition comprising a polysaccharide moiety of Formula I:

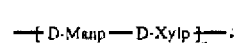
(I)

wherein D-Manp represents a D-mannopyranose moiety, D-Xylp represents a D-xylopyranose moiety, and n is about 5 to about 70; and one or more lipid moieties covalently linked to the polysaccharide moiety of Formula I or electrostatically associated with the polysaccharide moiety of Formula I. The antifreeze glycolipid compounds and compositions can be used for a variety of industrial, agricultural, medical, and cosmetic applications where recrystallization-inhibition, cryoprotection, or cryopreservation is desired. The antifreeze glycolipid compounds or compositions can be used as, for example, as cryoprotectants for tissue preservation and transplantation, improving the texture of processed frozen food and frozen meats, frostbite protection, crop protection, and green alternatives for land vehicle antifreeze and aircraft de-icing.

26 Claims, 11 Drawing Sheets